(12) United States Patent  
Chen et al.

(10) Patent No.: US 7,902,121 B2
(45) Date of Patent: Mar. 8, 2011

(54) MHC-ANTIGEN ARRAYS FOR DETECTION AND CHARACTERIZATION OF IMMUNE RESPONSES

(75) Inventors: Daniel Shin-Yu Chen, Burlingame, CA (US); Yoav Soen, Palo Alto, CA (US); Daniel Lewis Kraft, Stanford, CA (US); Patrick O. Brown, Palo Alto, CA (US); Mark Davis, Atherton, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1367 days.

(21) Appl. No.: 10/856,185

(22) Filed: May 27, 2004

(65) Prior Publication Data

US 2005/0019843 A1 Jan. 27, 2005

Related U.S. Application Data

(63) Continuation-in-part of application No. 10/190,425, filed on Jul. 2, 2002.

(60) Provisional application No. 60/303,109, filed on Jul. 2, 2001, provisional application No. 60/473,936, filed on May 27, 2003.

(51) Int. Cl.
*C40B 20/04* (2006.01)
*C07H 21/04* (2006.01)

(52) U.S. Cl. .......... 506/4; 506/2; 506/3; 506/33; 506/35; 435/286.3; 435/283.1; 435/305.2

(58) Field of Classification Search .................. 506/4, 2, 506/3, 33, 35; 435/286.3, 283.1, 305.2
See application file for complete search history.

(56) References Cited

U.S. PATENT DOCUMENTS

| 4,591,570 | A |   | 5/1986  | Chang |
|---|---|---|---|---|
| 5,635,363 | A | * | 6/1997  | Altman et al. ............... 435/7.24 |
| 6,140,113 | A |   | 10/2000 | Schneck et al. |
| 6,268,411 | B1 |   | 7/2001  | Schneck et al. |
| 6,448,071 | B1 |   | 9/2002  | Schneck et al. |
| 6,458,354 | B1 |   | 10/2002 | Schneck et al. |
| 6,579,970 | B2 | * | 6/2003  | Nicolette ..................... 530/328 |
| 7,022,483 | B1 | * | 4/2006  | Albani .......................... 435/7.1 |
| 2005/0037369 | A1 | * | 2/2005  | Neote et al. ..................... 435/6 |
| 2005/0054575 | A1 | * | 3/2005  | Schlom et al. .................. 514/14 |

FOREIGN PATENT DOCUMENTS

WO WO 00/63701 10/2000

OTHER PUBLICATIONS

Altman et al., Phenotypic Analysis of Antigen-Specific T Lymphocytes, (1996), Science, 274:94-96.
Belov et al., Immunophenotyping of Leukemias Using a Cluster of Differentiation Antibody Microarray, (2001), Cancer Research, 61:4483-4489.
Dal Porto et al., A Soluble Divalent Class I Major Histocompatibility Complex Molecule Inhibits Alloreactive T Cells At Nanomolar Concentrations, (1993), Proc. Natl. Acad. Sci., 90:6671-6675.
Ziauddin et al., Microarrays of Cells Expressing Defined CDNAS, (2001), Nature, 411:107-110.

* cited by examiner

*Primary Examiner* — T. D. Wessendorf
(74) *Attorney, Agent, or Firm* — Bozicevic, Field & Francis LLP; Pamela J. Sherwood

(57) ABSTRACT

T cells are profiled with respect to their expression of antigen receptor. The cells are arrayed on a planar or three-dimensional substrate through binding to immobilized or partially diffused MHC-antigen complexes. The cells may further be characterized with respect to their ability to respond to external stimulus in the microenvironment. External stimuli include cell-cell interactions, response to factors, and the like.

24 Claims, 14 Drawing Sheets

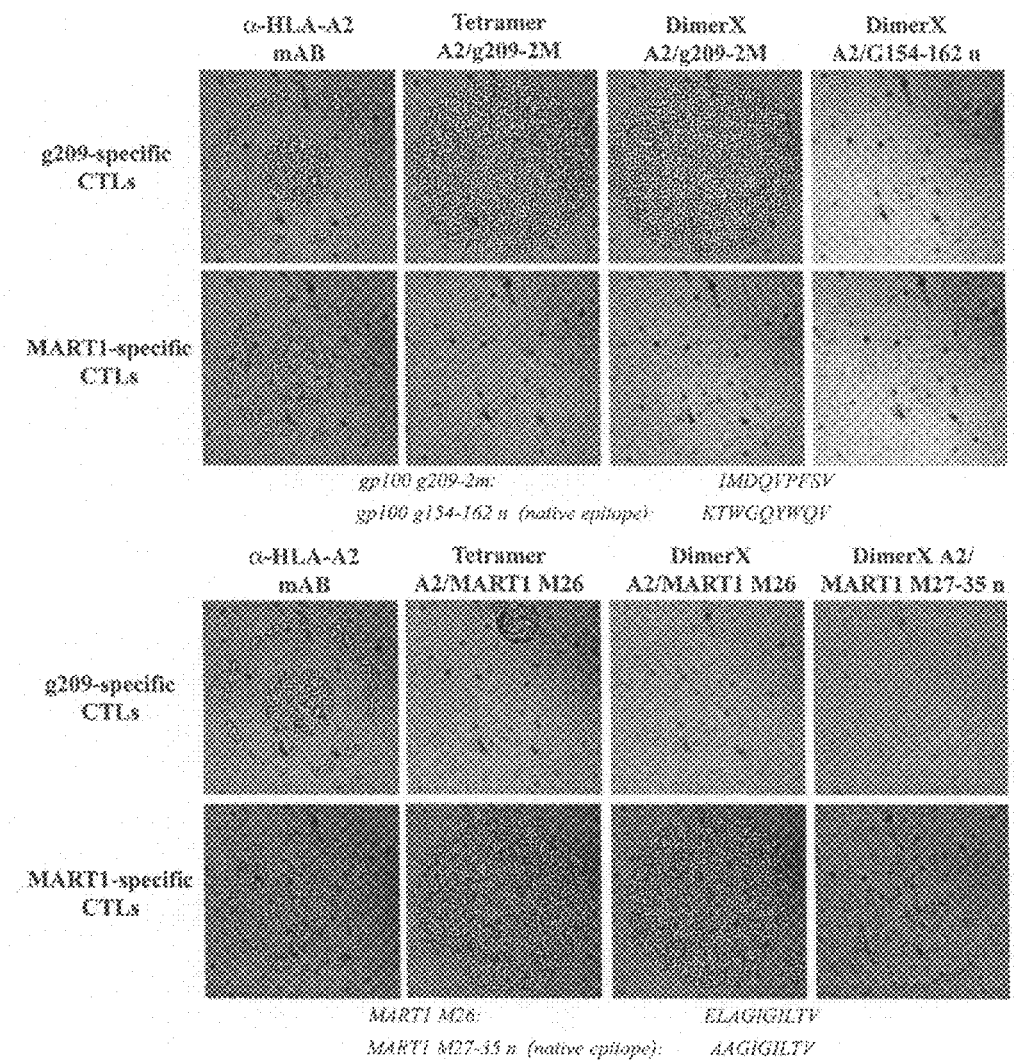

α-CD3     0.4ng           0.2ng           0.1ng         0.05ng
2.25ng                  OVA/K$^b$ tetramer FIGURE 8A
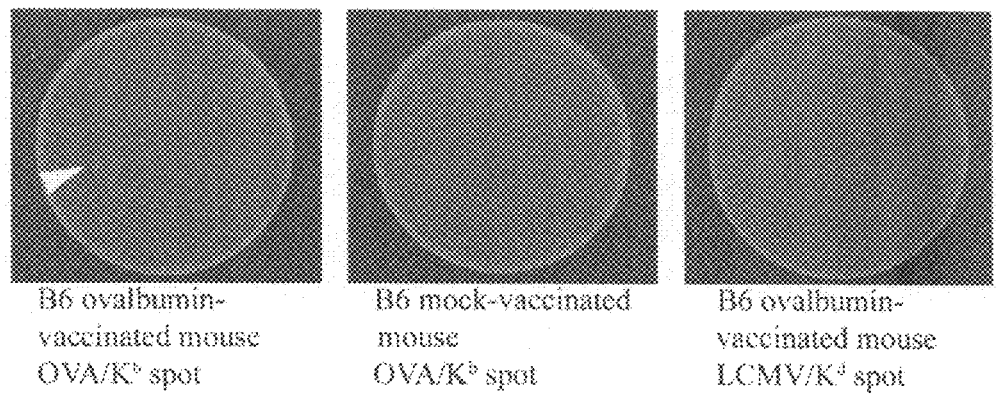
B6 ovalbumin-vaccinated mouse OVA/K$^b$ spot
B6 mock-vaccinated mouse OVA/K$^b$ spot
B6 ovalbumin-vaccinated mouse LCMV/K$^d$ spot
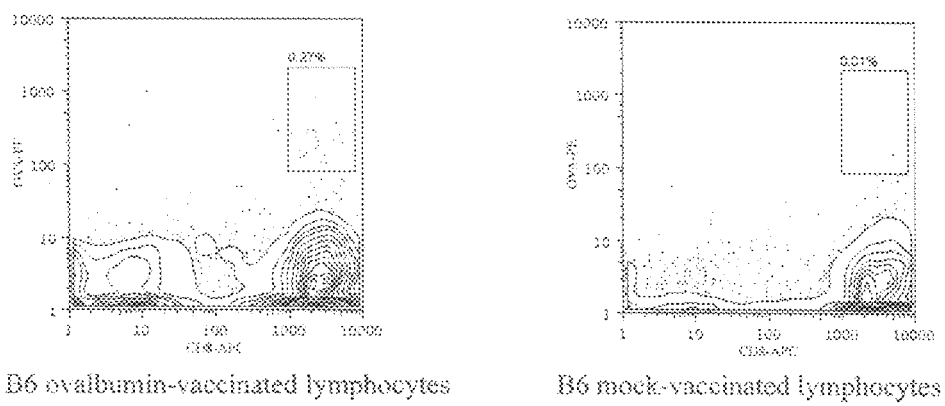
B6 ovalbumin-vaccinated lymphocytes
B6 mock-vaccinated lymphocytes
FIGURE 8B FIGURE 10A
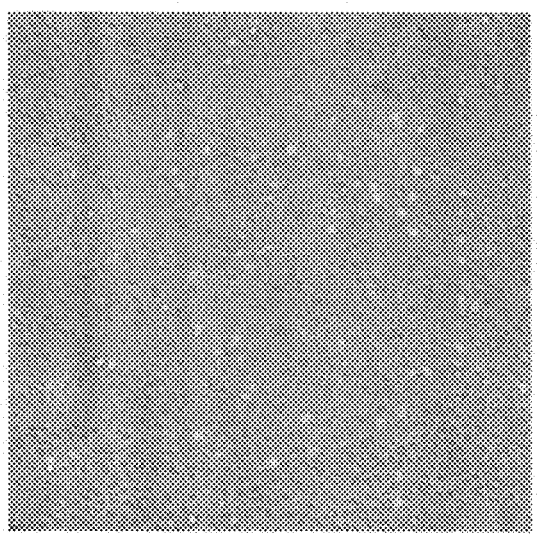
FIGURE 10C
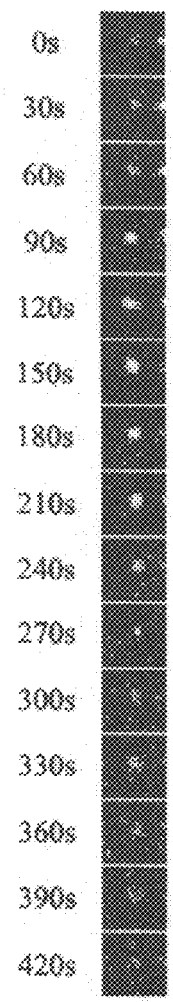
Figure 5B.
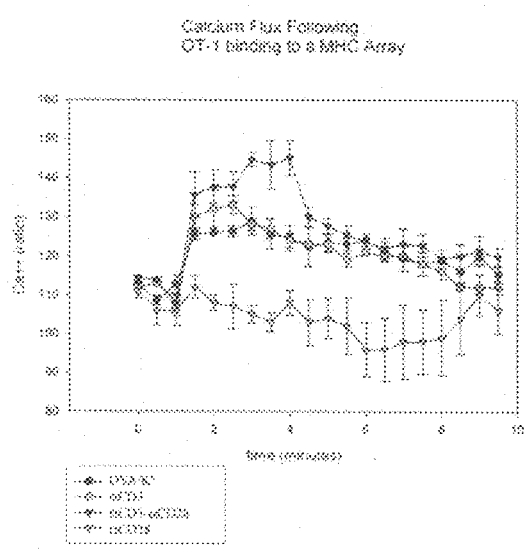
FIGURE 10B

|  | Tetramer A2/g209-2M | Tetramer A2/MART1 M26 |
|---|---|---|
| MB-2 gp100 specific CTL | 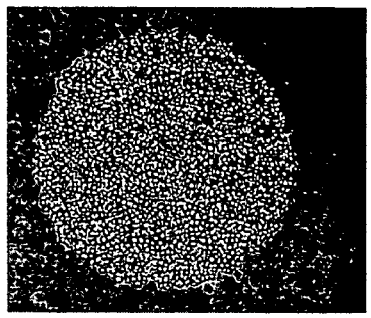 | 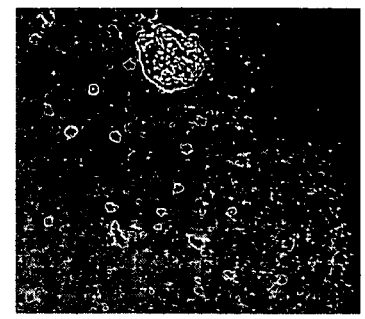 |
| 461.30 MART1 specific CTL | 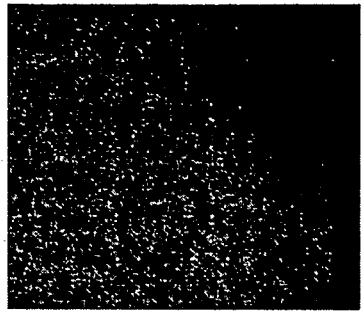 | 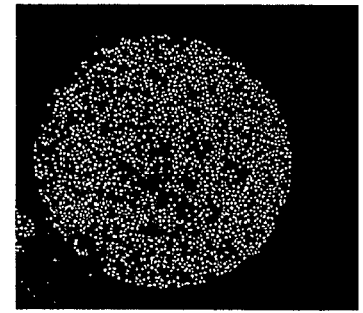 |
FIGURE 14

MHC-ANTIGEN ARRAYS FOR DETECTION AND CHARACTERIZATION OF IMMUNE RESPONSES

T cells are vitally important in the orchestration and execution of immune responses to infection, rejection of cancer cells, and control of potential autoimmune responses. It is therefore of considerable interest to evaluate the presence of T cells in various samples according to their antigenic specificity. For many years, the ability to identify T cells directly through their antigen receptor eluded scientists. Foreign antigens alone cannot be used to identify T cells because the receptor specificity is towards a complex of antigenic peptide bound to an MHC molecule, not the antigenic peptide itself. Further, the t½ for binding between the T-cell receptor and the MHC-peptide complex is so short that attempts to label T cells with monomeric MHC-peptide complexes have routinely failed. A breakthrough in labeling antigen-specific T cells came with the idea of making multimers of the MHC-peptide complex, so as to increase the avidity of the interaction.

Several approaches have been exploited in producing multimeric MHC-peptide complexes. In one approach, recombinant MHC molecules are biotinylated, often using the bacterial enzyme BirA, which recognizes a specific amino acid sequence. Avidin, or the bacterial counterpart streptavidin, contains four sites that bind biotin with extremely high affinity. Mixing the biotinylated MHC-peptide complex with avidin or streptavidin results in the formation of a tetramer. Routinely, the streptavidin moiety is labeled with a fluorochrome to allow detection of those T cells capable of binding the MHC-peptide tetramer.

Detection and characterization of specific cellular immune responses to cancer, microbial pathogens, allergens and autoantigens have been greatly aided by the ability to visualize and isolate specific T cell populations using multimeric MHC-peptide constructs. However, the current methodology, utilizing flow cytometry, immunohistochemistry, or in situ staining is technically difficult, expensive and time consuming. Methods that allow rapid, high-throughput analysis of antigenic specificity in populations of T cells are of great interest for a variety of research and clinical applications.

RELATED PUBLICATIONS

A protein microarray is described in International Patent Application WO00/63701. U.S. Pat. No. 4,591,570 discloses a matrix of antibody coated spots for determination of antigens. Immunophenotyping of cells using an antibody microarray is discussed in Belov et al. (2001) Cancer Research 61:4483-4489. Microarrays of cells expressing defined cDNAs are discussed in Ziauddin et al. (2001) Nature 411:107-110.

The synthesis and use of MHC-peptide tetramers is described in Altman et al. (1996) Science 274:94-96, and in U.S. Pat. No. 5,635,363. The "Dimerx" technology is described by Dal Porto et al. (1993) Proc. Natl. Acad. Sci. USA. 90:6671-6675; and in Schneck et al., U.S. Pat. Nos. 6,268,411; 6,140,113,6,448,071; and 6,458,354

SUMMARY OF THE INVENTION

Compositions and methods are provided for profiling of T cells, in which cells are profiled with respect to their expression of antigen receptors, and ability to respond to external stimulus in the microenvironment. External stimuli include cell-cell interactions, response to factors, and the like. The cells are arrayed on a planar or three-dimensional substrate through binding to immobilized or partially diffused MHC-antigen complexes. Additional probes may also be arrayed in combination with the MHC-antigen complexes, including signaling cues that act to regulate cell responses, adhesion molecules, differentiation factors, etc. After the cells are arrayed, they may be characterized for expression of antigen receptor and other phenotypic attributes, e.g. expression of other cell surface markers; or maintained in culture for a period of time sufficient to determine the response to a stimulus of interest.

Each of the arrayed MHC-peptide complex "spots" forms a multivalent plane of antigen, e.g. viral antigen, autoantigen, tumor associated antigen, etc., presented in the context of a specific MHC molecule. This array is used to select those T cells in a complex population that are capable of binding that antigen. For example, a library of immobilized MHC-peptide constructs can be used to test a blood or tissue sample for the presence of antigen-specific T cells, or diagnose clinical pathology based upon presence of particular antigen-specific T cell populations. In another embodiment, an array of MHC-peptide complexes is used for the identification of novel MHC-restricted epitopes.

The methods of the invention allow for passive and active profiling of many cells in parallel, programmed patterning of specific cell types, high-throughput stimulation of cells by a variety of immobilized or diffused cues, which may be deposited in any combination and/or concentration, followed by phenotype examination and/or screening, and studies of cell-cell and cell-ECM interactions.

The ability to specifically capture cells onto defined locations at resolutions and feature sizes that are close to cellular dimensions allows for programmed cell patterning and enables close juxtaposition of different cell types, so that their mutual interaction can be examined. These features make the cell arrays suitable for studying cell-cell and cell-ECM interactions, and for cell migration assays, secretion assays, and active and passive profiling assays. The array can optionally be incorporated into a multi-well-based platform by creating arrays within wells.

The printed peptide-MHC tetramer spots contain phycoerythrin (PE) fluorescent dye, which allows visualization of peptide-MHC spot borders.

Figure 3:
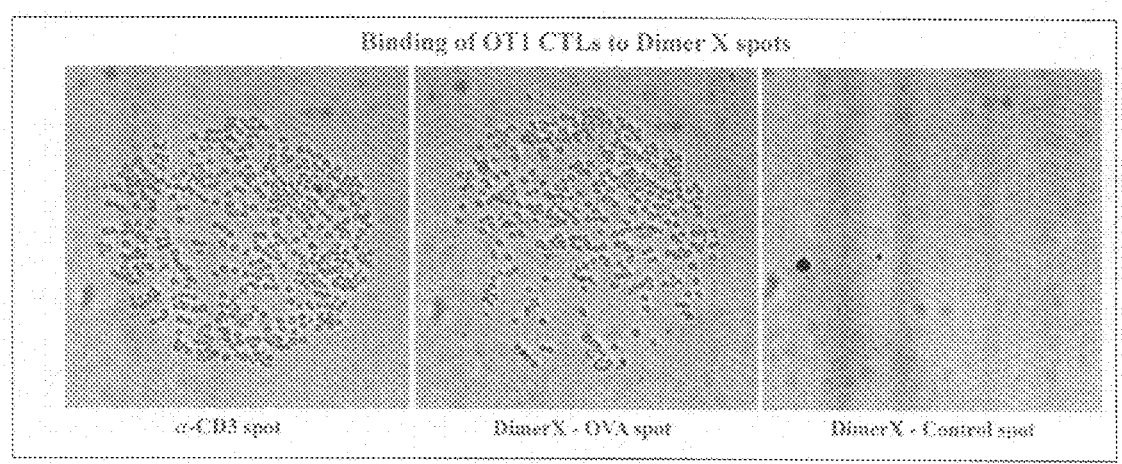

FIG. 3. Specific binding of OT1 CTLs to a DimerX-OVA spot following 10' incubation at 20° C. Shown are three DIC 10× images taken from regions printed with α-CD3 spot (left image), DimerX-OVA peptide (middle), and DimerX-control peptide (right).

FIG. 4. MHC-peptide array detection of human melanoma-specific CTLs. gp100/g209-specific and MART1-specific tumor infiltrating cells (TILs) were FACS-sorted from melanoma patients undergoing peptide vaccination with melanoma tumor antigens gp100 and MART-1. The cells were re-stimulated in vitro with peptide-pulsed APCs (JY), PHA and 50 μ/ml IL-2, and frozen in aliquots. One aliquot of each was thawed and applied (separately) to duplicate, arrays on the same slide. The array contained: (i) heteroclytic tetramers and DimerX for both the gp100 and MART1 antigens, (ii) DimerX with native gp100 and MART1 antigens, antibody against the relevant tissue type (HLA-A2), and (iii) several other antibodies against T cell surface markers. $4 \times 10^6$ gp100/g209- and MART-1 specific CTLs were incubated on independent replicates of the same array on the same slide for 30' at 37° C. Non-attached cells were subsequently washed with RPMI. The resulting binding pattern reveals exclusive binding of the gp100/g209-specific cells to both the DimerX and tetramer gp100/g209 constructs ($1^{st}$ and $3^{rd}$ rows from the top). Similarly, the MART1-specific cells only bind the MART1 tetramer and DimerX constructs ($2^{nd}$ and $4^{th}$ rows from the top).

Figure 5A:
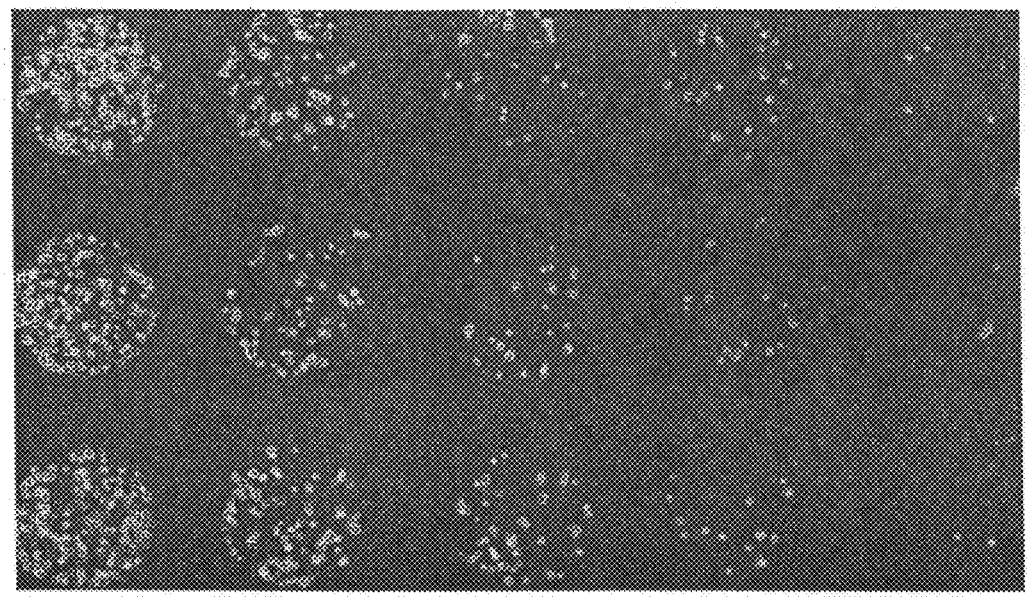
Figure 5B:
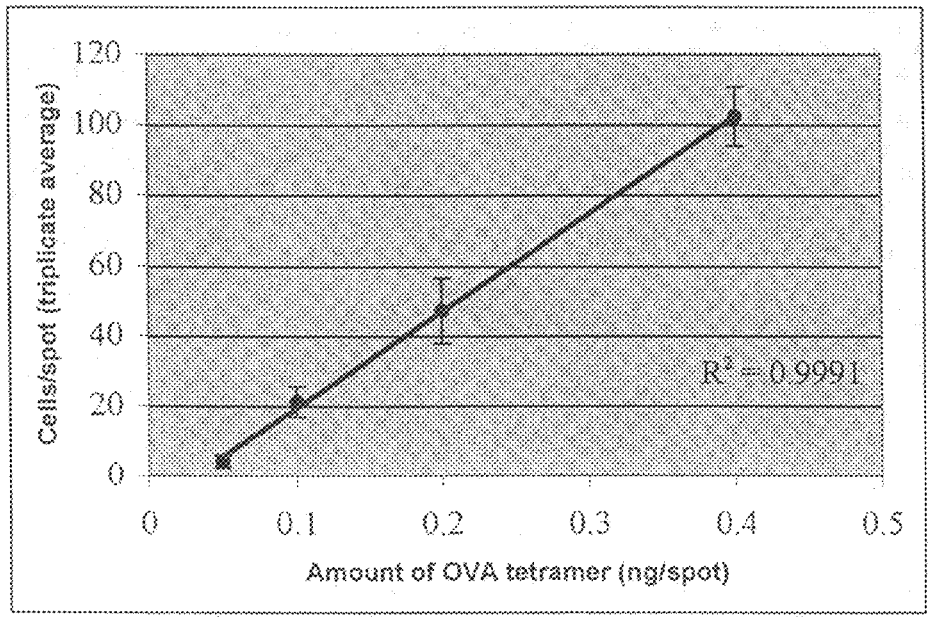

FIGS. 5A-B. Binding of OT-1 lymphocytes to a serial dilution of OVA/$K^b$ tetramer. The effect of tetramer dilution on cell capture was tested by examining the binding of OT-1 lymphocytes to a serial dilution of immobilized OVA/MHC tetramer. The cells were suspended at a concentration of $2.5 \times 10^6$/ml and incubated on the array for 30 minutes at room temperature. Following the removal of unbound cells, the array was imaged and scored for the number of OT-1 cells on each of the spots. A. A reconstruction of the relevant array region by a patchwork of 10× images, revealing a monotonic reduction in the number of bound cells with tetramer dilution. Amount of MHC tetramer deposited is given in nanograms per spot B. In this specific example, the number of immobilized OT-1 lymphocytes on the OVA/$K^b$ spots was linearly dependent on the amount of tetramer deposited. Averaged cell numbers and standard errors are based on triplicate spots. The line represents a linear fit to the data.

FIG. 6A-B. Detection and sorting of a rare (1%) cell population using a specific MHC-peptide tetramer spot. Shown are binding results to several spots on two isolated array replicates, both printed on a single Hydrogel slide A. A control experiment performed on one array replicate without the rare cell population. Note the low number of cells that bind the MCC spot (top panel). B. A differential binding experiment with 1% of Cy5-labeled 5CC7 lymphocyte (red) and 99% of FITC-labeled B10A splenocytes (green), demonstrating that despite the low abundance of 5CC7cells, the correct MHC-peptide spot (MCC) still captures enough cells to validate their presence in the mixture (compare, for example, with the corresponding spot in the control experiment on A.).

Figure 7A:
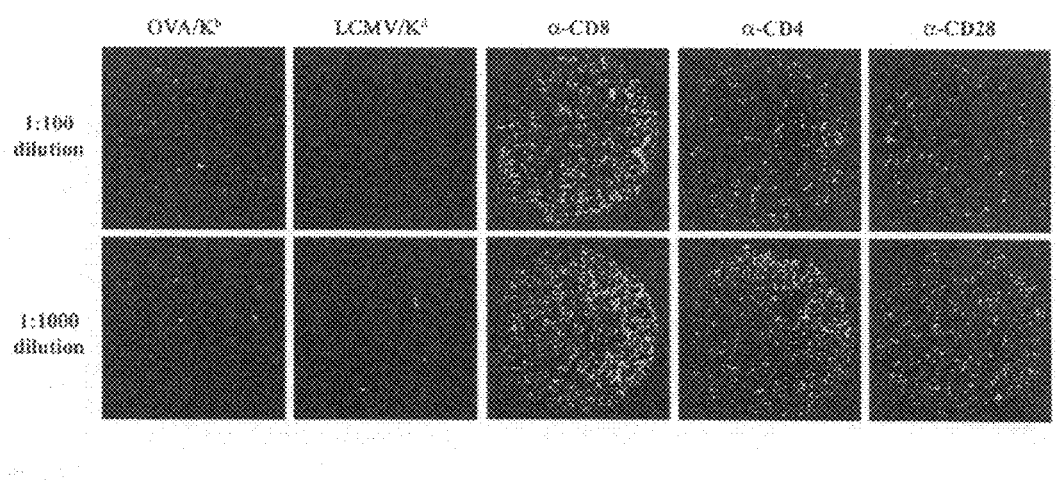
Figure 7B:
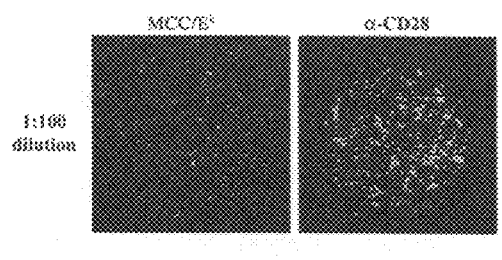

FIGS. 7A and 7B. Sensitivity of peptide-MHC tetramer-mediated detection of OVA-specific CTLs and MCC-specific helper T cells. A. DiD-labeled OT-1 OVA-specific cells (red) were diluted 1:100 (top panels) or 1:1000 (bottom panels) in DiO-labeled, monocyte-depleted, B6 mouse lymph node cells (green). $2.7 \times 10^4$ (top panels) and $4.41 \times 10^3$ (bottom panels) of DiD-labeled OT-1 cells were mixed with $2.7 \times 10^6$ and $4.41 \times 10^6$ of DiO-labeled CD11b-depleted lymph node cells, respectively. The different dilutions were applied to identical, but separate arrays printed with OVA/$K^b$, and MCC/$E^k$ tetramers, LCMV/$K^d$ control tetramer and three different antibody spots (α-mouse CD8, α-mouse CD4, and α-mouse CD28). Following 10' incubation at 37° C., the cells were washed in RPMI and the slide was scanned. Shown are the OT-1 (red) and lymph node (green) cells that were captured by the OVA tetramer (left), LCMV tetramer (second left), and the antibody spots. B. Class II MHC-mediated detection and sorting of helper T cells. $3.5 \times 10^4$ DID-labeled 5c.c7 lymphocytes (red) were diluted 100-fold in $3.6 \times 10^6$ B10A DIO-splenocytes (green). The mixed suspension was incubated at 37° C. for 10 minutes prior to wash with RPMI. Shown are the 5c.c7 sells (red) and splenocytes (green) captured by the MCC (left) and α-CD28 (right) spots.

FIG. 8A-B. Detection of a weak immune response to vaccination. CTLs from Ova-vaccinated and mock-vaccinated mice were analyzed in parallel using an MHC-array and flow cytometry analysis. Mice received base-of-tail injections of ovalbumin/Freund's Adjuvant emulsions or phosphate buffered saline (mock)/Freund's adjuvant on day 0and day 7. Draining lymph nodes were harvested on day 11, dissociated into a single cell suspension, and A. CTLs were enriched on a α-CD8-bead column. $2 \times 10^6$ and $3.2 \times 10^6$ cells from the Ovalbimin- and mock-vaccinated mice, respectively, were incubated on identical, but separate arrays printed with OVA/$K^b$ tetramer, LCMV/$K^d$ (control) tetramer and various antibodies. The three panels show the relevant array results. A rare population of cells from the ovalbumin-vaccinated mouse was captured on the OVA/$K^b$ (left), but not on the LCMV/$K^d$ (right) tetramer spot. The cells captured on the OVA/$K^b$ tetramer spot were CD8-positive (as determined by counter-staining using a α-CD8-FITC monoclonal antibody on the array). An arrowhead points to some of the cells that were bound to that spot. The cells from the mock-vaccinated mouse did not bind the OVA tetramer (middle spot) or the LCMV/$K^d$ tetramer. Spot regions are marked with a blue color by overlaying the tetramer's PE fluorescent signal onto the DIC image. B. FACS analysis of the cells from the ovalbumin-vaccinated (left panel) and mock-vaccinated mice (right). 0.27% of the total CD8$^+$ cells from the vaccinated mouse co-stain with OVA/$K^b$, compared with 0.01% in the mock-vaccinated mouse.

Figures 9A, 9B:
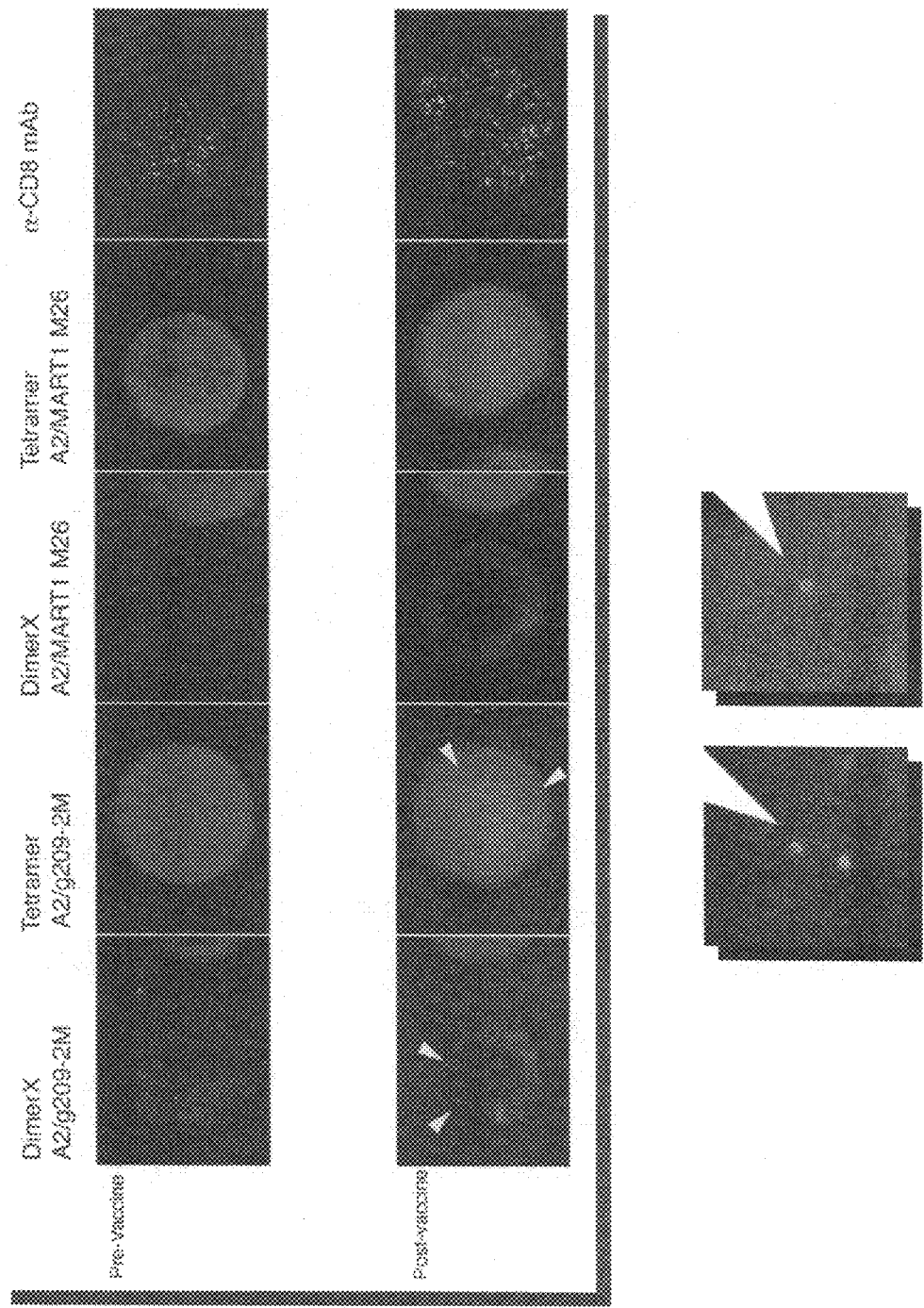

FIG. 9A-B. Detection of induced, melanoma-antigen-specific cellular immune response in a melanoma patient. A patient with recurrent resected stage 3 malignant melanoma receiving gp100, MART-1 and tyrosinase peptide vaccinations on day 0 (pre-vaccine), day 14 and day 28 (post-vaccine) developed a persistent local inflammatory reaction to the gp100 peptide vaccine. CD8$^+$ lymphocytes were isolated from peripheral blood mononuclear cells (PBMC) collected on day 0, 14 and 28 by positive selection on an α-CD8 magnetic bead column. $2 \times 10^5$ CD8$^+$ lymphocytes were applied to an array of DimerX and tetramer constructs, incubated for 12 hours at 4° C., washed ×2 in RPMI, and counterstained with FITC α-CD8 mAb (green) and fixed in 4% paraformaldehyde. PE fluorescence (red) and low level of FITC auto-fluorescence (green) marks the tetramer and DimerX positions, respectively. A. CD8$^+$ lymphocytes isolated prior to vaccination (top panels) or 2 weeks after vaccination did not bind any of the spots. By contrast, cells isolated 4 weeks after vaccination were immobilized on both the gp100 (g209-2M) DimerX (bottom left) and gp100 (g209-2M) tetramer-SA-PE (second left) spots. Yellow arrows point at two among the several CD8$^+$ lymphocytes that were immobilized on the gp100 (g209-2M) constracts. B. Magnification of asterix-arrowheads in FIG. 9A.

FIGS. 10A-C. Activation of OT-1 lymphocytes following an exposure to pre-printed spots on a MHC array. OT-1 lymphocytes were pre-loaded with fura-2 dye for 20 minutes at room temperature prior to exposure to the cellular microarray (time zero). The cells were incubated at 37° C., 5% $CO_2$ and fluorescence intensities at 340 and 380 nm were measured every 30 seconds from each of the spots on the array. Calcium flux signal was triggered in the OVA-specific cells as soon as they reached the OVA/$K^b$ tetramer spots, the activating antibody spots (α-CD3 and α-CD3/α-CD28), but not the irrelevant MCC/$E^k$ tetramer or the non-activating antibody spots (e.g. α-CD28). A. Calcium flux signal (yellow) overlaid onto a 10× DIC image of OT-1 cells on a combined, FITC-labeled α-CD3/α-CD28 spot. Fura-2 fluorescence intensity ratios are represented in pseudo-color and the overlaid spot region (blue) is determined from the FITC image. Note that the spot pattern can be inferred from the fure-2 signal representing activation, even without removing unbound cells. B. A time-lapsed series of images taken of a representative OT-1 lymphocyte specifically immobilized onto an OVA/$K^b$ spot. The cell undergoes a rapid, transient calcium flux as measured by fura-2 fluorescence. C. Averaged calcium flux traces (n=3) recorded from an OVA/$K^b$ spot (purple circles), α-CD3/α-CD28 spot (brown triangles), α-CD3 spot (green circles), and a non-activating, α-CD28 spot (orange triangles). Error bars represent calculated standard error of mean.

Figure 11:
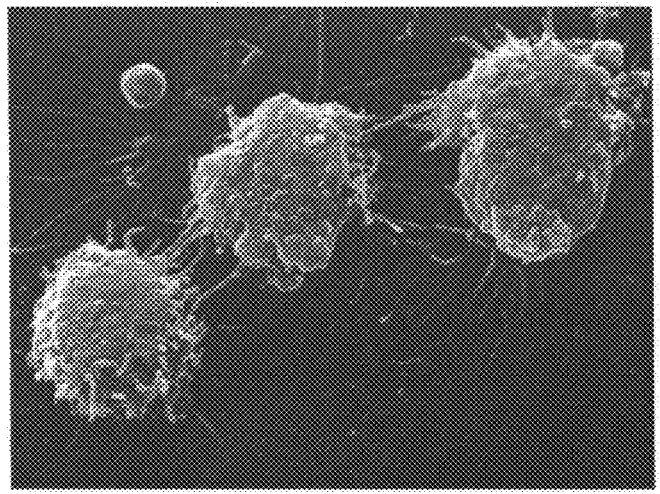

FIG. 11. Scanning electron micrograph (6200×) of human gp100-specific $CD8^+$ lymphocytes that were immobilized by a heteroclytic gp100 tetramer spot.

Figure 12:
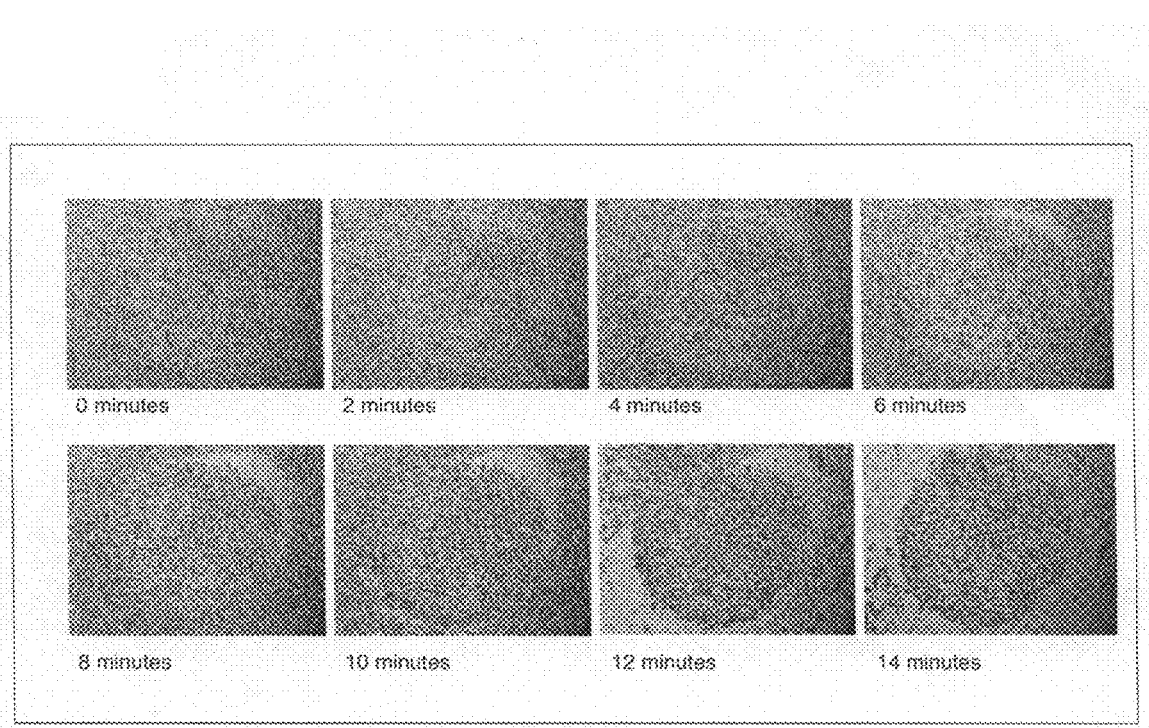

FIG. 12. Evaporation-induced spot formation. $4 \times 10^5$ OVA-specific CTLs were. applied (at time zero) to a MHC array and incubated at room temperature for 14'. Time lapsed video microscope DIC images are shown every 2 minutes. Spontaneous, evaporation-induced cellular movements lead to removal of cells outside the hOVA/$h2k^b$ spot boundary and to the formation of an isolated cell cluster inside the spot.

Figure 13:
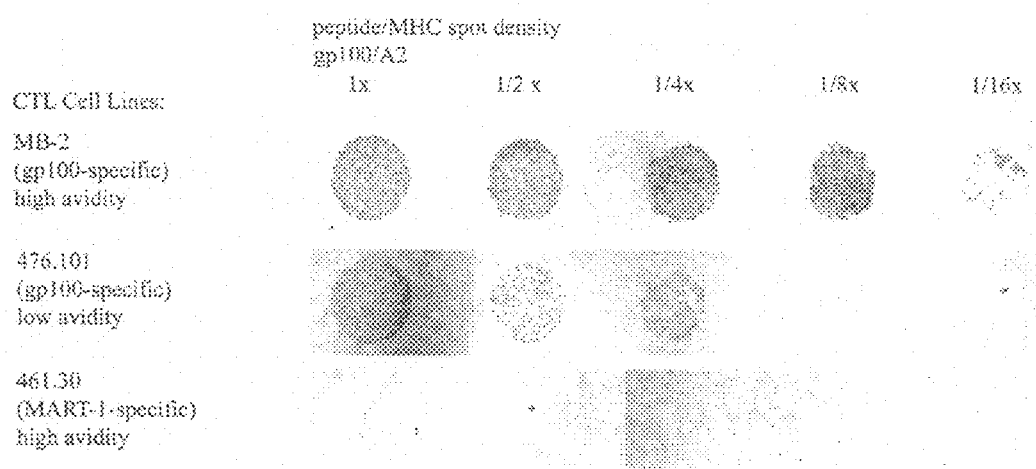

FIG. 13. Peptide/MHC concentration compensates for low avidity. Three human CD8+ lymphocytes specific for melanoma-associated antigens are expended from HLA-A2 patients with malignant melanoma and incubated separately with identical arrays which include a dilution series of gp100-2M peptide (IMDQVPFS)/HLA-A*0201 tetramers (the 1× print used 4.3 nl of 0.25 mg/ml peptide/MHC). MB-2 and 476.101 cells are specific for gp100-2M/A2 and 461.30 is specific for MART M26 (ELAGIGILTV)/A2. Differences in binding characteristics are reflective of differences in avidity for cognate peptide/MHC. Despite the relatively low avidity of 476.101 cells, increased gp100-2M/A2 concentration leads to a confluent spot of captured cells.

FIG. 14. Specificity of peptide/MHC capture is peptide-specific regardless of T cell activation sate or MHC context. In vitro activated human CD8+ lymphocyte clones MB-2 and 461 were incubated on duplicate microarrays which include gp100-2M/HLA-A2and MART-1 M26/HLA-A2 tetramer spots. MB-2 bound only to gp100 spots and 461.30 bound only to MART-1 spots.

DETAILED DESCRIPTION OF THE EMBODIMENTS

MHC-antigen profiling arrays allow T cells to be characterized with respect to their expression of antigen receptor. The cells are arrayed on a planar or three-dimensional substrate through binding to immobilized or partially diffused MHC-antigen complexes, where the complexes have an avidity sufficient to provide stable binding of the cells. After the cells are arrayed, they may be characterized, or maintained in culture for a period of time sufficient to determine the response to a stimulus of interest.

The methods and compositions are useful in a variety of clinical and research applications. Such applications include the detection and/or quantitation of T cells in a sample that have antigenic specificity for an antigen of interest, which may include tumor antigens; viral antigens, bacterial antigens; parasitic antigens; environmental antigens; allergens; autoimmune antigens; etc. Samples may be clinical samples, e.g. blood, lymph, cerebrospinal fluid, synovial fluid, and the like, where T cells may be found. Other samples of interest include cultured cells, e.g. which may be exposed to experimental conditions of interest.

The T cell profile may be used in diagnosis or prognosis of an immune response, e.g. response to foreign antigens, autologous antigens, allogeneic antigens, xenogeneic antigens, etc. T cell populations may be tested and/or compared for responsiveness to a condition of interest, where such conditions may include exposure to an antigen; exposure to cytokines, chemokines, interleukins, and other factors; alterations in environment such a media, temperature, pH, presence of other cells, and the like. T cells may be profiled for expression of cell surface markers in addition to the antigen receptor, e.g. markers involved in activation and effector functions. An arrayed library of MHC-peptide complexes can be used for the identification of novel MHC-restricted epitopes and/or responses to thereof. The methods are also useful in selecting T cells having a desired antigen specificity, which may then be expanded for various purposes. Methods of expansion include the use of growth factors, cytokines, cell adhesion molecules, extracellular matrix material, and the like.

The use of a variety of surfaces and printing methods is also provided. In one embodiment of the invention, the substrate for the array is a hydrated, deformable hydrogel. Included are polyacrylamide hydrogels, preferably comprising components that weakly repulse cells, thereby providing low background binding. In one embodiment, the substrate comprises a polymerized mixture including acrylamide, and hydrophilic acrylates. In one embodiment of the invention, probes are printed on the substrate with a non-contact printer.

Different MHC-peptide concentrations can be used in an array to sort T cells according to their level of TCR expression; activity; and/or affinity to the bound MHC-peptide complexes. Altering the cell concentration in samples applied to the array, a scaling curve may be constructed that is useful in translating differences in the number of captured cells to differences in the frequency of antigen-specific cells.

MHC complexes of interest provide specific binding partners (capture probes) for the T cell antigen receptor. The complexes may be arrayed at a range of concentrations, as one or a combination of molecules. Usually each location on an array will include at least one MHC-antigen binding complex, which are optionally combined with secondary probes. The "printing" of complexes, by which it is intended that a complex is placed on the solid or soft substrate in a specific location and amount, may be used to direct cell binding; patterned assembly; migration; and programming of multicellular structures.

The binding complex may have a wide variety of peptide-MHC combinations. Class I MHC molecules will usually be used to bind $CD8^+$ T cells, and class II will usually be used to bind $CD4^+$ T cells. Non-classical MHC molecules can also be used. The MHC-antigen binding complex comprises monomers or multimers of: an α MHC subunit, a β MHC subunit, and a peptide antigen bound in the cleft formed by the α and β subunits. Complexes of interest may be monomeric, dimeric, trimeric, tetrameric, or higher. In addition, different MHC-peptides can be pooled and spotted together or alternatively, different peptides can be pooled prior to their incorporation into the MHC complex. Such pooled constructs can be useful for screening large epitope libraries by iterations (e.g. initial screening with pooled peptides to find positive spots, which are then followed-up by separately reprinting only those peptides that appear in the positive spots). The MHC proteins may be from any mammalian or avian species, e.g. primate sp., particularly humans; rodents, including mice, rats and hamsters; rabbits; equines, bovines, canines, felines; etc. Of particular interest are the human HLA proteins, and the murine H-2 proteins. Included in the HLA proteins are the class II subunits HLA-DPα, HLA-DPβ, HLA-DQα, HLA-DQβ, HLA-DRα and HLA-DRβ, and the class I proteins HLA-A, HLA-B, HLA-C, and $β_2$-microglobulin. Included in the murine H-2 subunits are the class I H-2K, H-2D, H-2L, and the class II I-$A^α$, I-$A^β$, I-$E^k$, I-$E^α$ and I-$E^{62}$, and $β_2$-microglobulin. Usually the MHC protein subunits are soluble forms of the membrane-bound protein. Optionally the complexes are labeled. Methods of producing such complexes are known in the art.

The antigenic peptide will be from about 6 to 12 amino acids in length for complexes with class I MHC proteins, usually from about 8 to 10 amino acids. The peptide will be from about 6 to 25 amino acids in length for complexes with class II MHC proteins, usually from about 10 to 20 amino acids. The peptides may have a sequence derived from a wide variety of proteins. In many cases it will be desirable to use peptides that act as T cell epitopes. The epitopic sequences from a number of antigens are known in the art. Alternatively, the epitopic sequence may be empirically determined, by isolating and sequencing peptides bound to native MHC proteins, by synthesis of a series of peptides from the target sequence, then assaying for T cell reactivity to the different peptides, or by producing a series of binding complexes with different peptides and quantitating the T cell binding. The peptides may be prepared in a variety of ways as known in the art.

The peptide MHC complex may be multimerized through fusion to a multivalent protein, e.g. immunoglobulin, or by binding the monomers to a multivalent entity through specific attachment sites. A multimer may also be formed by chemical cross-linking. The attachment site for binding to a multivalent entity may be naturally occurring, or may be introduced through genetic engineering. The site can be a specific binding pair member or one that is modified to provide a specific binding pair member, where the complementary pair has a multiplicity of specific binding sites. Binding to the complementary binding member can be a chemical reaction, epitope-receptor binding or hapten-receptor binding where a hapten is linked to the subunit chain. One of the subunits can be fused to an amino acid sequence providing a recognition site for a modifying enzyme, for example BirA, various glycosylases, farnesyl protein transferase, protein kinases and the like. The subunit may be reacted with the modifying enzyme at any convenient time, usually after formation of the monomer. The group introduced by the modifying enzyme, e.g. biotin, sugar, phosphate, farnesyl, etc. provides a complementary binding pair member, or a unique site for further modification, such as chemical cross-linking, biotinylation, etc. that will provide a complementary binding pair member. Commercially available complexes include biotinylated complexes bound to streptavidin or avidin; and immunoglobulin fusion proteins.

In addition to the MHC-antigen binding complex, probes may be provided on the array that generate signals or affect the cell's growth, phenotype, viability, and the like may be used, and can be bound to the array substrate, partially diffused on the substrate, present in the medium, etc. Such probes, which may be referred to as "signaling probes", include a variety of polypeptides and other biologically active molecules, e.g. chemokines, cytokines, growth factors, differentiation factors, drugs, polynucleotides, etc. Signaling probes of interest include, without limitation, ICAM, anti-CD28 Mab, cytokines, peptides, lipids, lipid bilayers, cell extracts, and the like. In addition to immobilized probes, soluble factors can be brought into contact with the immobilized cells, e.g. antibodies, such as anti-CD28 Mab, cytokines, Immunomodulatory agents, and the like.

By providing for a controlled selection and position of cells, the signals, microenvironments and conditions that provide for a specific phenotype, developmental path, or activation pathway can be explored in a systematic rigorous manner, in specific cell types. Such pathways can include, for example, stimulation of cells by proteins, other environmental cues, direct cell to cell contact, and the like, and may also include two way communication between cells of interest. The arbitrary choice of printed cues allows for reconstruction of well-defined micro-environments that can mimic essential features exhibited by their in vivo counterparts, thereby serving as simplified model systems for studying their interactions with cells. By controlling the dose of a printed signaling probe, activation and response curves for specific cell types can be mapped out, and the events following activation can be imaged. Systematic mixing of cues may reveal the synergistic structure of a specific process. Likewise, collecting data in parallel from a comprehensive set of defined, naturally occurring signaling cues can lead to understanding of the "language" utilized by cells.

Cell-arrays offer advantages over existing approaches for characterization of T cells. The current methodology, utilizing flow cytometry, immunohistochemistry, or in situ staining can be technically difficult, expensive and time consuming, and most importantly, limited to one, or at best, very few tetramers at a time. These drawbacks severely limit the ability to diagnose an immune response as well as to identify novel MHC-restricted epitopes, both of which would typically require screening a sample against a library of MHC-restricted antigens. The MHC-cell-array offers a screening platform for detection of immune responses and discovery of novel MHC-restricted epitopes. It also has the potential for "profiling" a patient's T-cell repertoire using very large arrays of diverse peptides. The profile obtained may be more informative than single measurements. In addition, the array format provides opportunities for exploring the functional properties of the cells, and their ability to respond to signaling cues. In addition, the techniques of the invention offer a higher throughput than existing phenotyping methods, and are faster, simpler and cheaper.

Definitions

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. As used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Substrate.

As used herein the term "substrate" refers to any surface to which the probes are arrayed in defined, specific geographic locations. The array may comprise a plurality of different probes, which are patterned in a pre-determined manner, including duplicates of single probe types and combinations of different probes in a given spot.

In one embodiment of the invention, the substrate for the cellular microarray provides a high binding capacity for the spotted probe; may allow for probe localization with negligible diffusion; has a very low background binding for cells, and may provide for weak repulsion of cells; and provides an environment that does not adversely affect cell behavior or expression. A hydrated substrate can be desirable, as cells tolerate manipulation better in such an environment, and printed probes are exposed to a less caustic environment, protecting against a change in the characteristics of each spotted probe.

In applications that require high specificity of binding, a preferred substrate for the array is a hydrated, deformable hydrogel. Included as substrates are polyacrylamide hydrogels, preferably comprising components that weakly repulse cells, thereby providing low background binding. Hydrophilic components find use for this purpose. In one embodiment, the substrate comprises a polymerized mixture including acrylamide, and hydrophilic acrylates, which may be referred to herein as a high specificity substrate, or high specificity hydrogel.

Such high specificity substrates may be characterized in terms on non-specific cell binding, e.g. binding of cells to the substrate in the absence of a capture probe; binding of cells that are not reactive with a capture probe, and the like. Such non-specific binding is usually less than about 100 cells/cm$^2$, more usually less than about 10/cm$^2$, and may be less than about 1/cm$^2$. Those of skill in the art will understand that cells vary in their ability to adhere to a substrate; for example the non-specific binding of macrophages and monocytes may be much greater than the non-specific binding of lymphocytes. In general, adherent cells will tend to higher background "stickiness" than non-adherent cells.

The high specificity hydrogel substrate provides for hydration to bound cells and probes, high probe loading capacity, lack of diffusion of bound probes, low background binding of cells and free flow of cells across the surface of the microarray due to weak cell repulsion. Cells immobilized by spotted probe on this surface can continue to function in a physiologic manner, secreting factors and spreading out as visualized by electron microscopy.

A variety of other solid supports or substrates find use in the methods of the invention, including both deformable and rigid substrates. By deformable is meant that the support is capable of being damaged by contact with a rigid instrument. Examples of deformable solid supports include hydogels, polyacrylamide, nylon, nitrocellulose, polypropylene, polyester films, such as polyethylene terephthalate, etc. Also included are gels, microfabricated or bioengineered surfaces, microchannels, microfluidics, chambers, and patterned surfaces, which allow cells to reside in a three-dimensional environment, while still being completely or partially exposed to potentially immobilized or diffused probes (hydrogels, collagen gels, matrigels, ECM gels, etc). Herein, we refer to such realization as a 3D-array. Rigid supports do not readily bend, and include glass, fused silica, nanowires, quartz, plastics, e.g. polytetrafluoroethylene, polypropylene, polystyrene, polycarbonate, and blends thereof, and the like; metals, e.g. gold, platinum, silver, and the like; etc.

In addition, a rigid or deformable support may also incorporate a multi-electrode-array for electrical recording and stimulation or any other construct of interest onto which cues could be dispensed. Such a support may also incorporate the means to generate an electrical, magnetic field which may allow the cells to be repulsed from or attracted to the surface of the array, or agitated to increase individual cells to more regions or provide shear for adherent cells. Surfaces may also present biochemical attachment sites to immobilize and/or orient spotted probes.

Derivitized and coated slides are commercially available, or may be produced using conventional methods. For example, SuperAldehyde™ substrates contain primary aldehyde groups attached covalently to a glass surface. Coated-slides include films of nitrocellulose (FastSlides™, Schleicher & Schuell), positively-charged nylon membranes (CastSlides™, Schleicher & Schuell), hydrogel matrix (HydroGel™, Packard Bioscience, CodeLink, Amersham), and simulated biologic surfaces (SurfaceLogix) etc.

The substrates can take a variety of configurations, including filters, fibers, membranes, beads, blood collection devices, particles, dipsticks, sheets, rods, capillaries, etc., usually a planar or planar three-dimensional geometry is preferred. The materials from which the substrate can be fabricated should ideally exhibit a low level of non-specific binding during binding events, except for methods where wide spectrum binding is preferred. Also, for functional profiling and manipulation experiments, the substrate should preferably be compatible with prolonged cell attachment and culturing.

In one embodiment of the invention, the substrate comprises a planar surface, and the binding members are spotted on the surface in an array. The binding member spots on the substrate can be any convenient shape, but will often be circular, elliptoid, oval or some other analogously curved shape. The spots can be arranged in any convenient pattern across or over the surface of the support, such as in rows and columns so as to form a grid, in a circular pattern, and the like, where generally the pattern of spots will be present in the form of a grid across the surface of the solid support. In some applications, labeled-probes are attached on and/or embedded in a substrate in a random order and their individual positions are inferred by analyzing their labels.

Array Preparation.

The subject substrates can be prepared using any convenient means. One means of preparing the supports is to synthesize and/or purify probes, and then deposit the probes as a spot on the support surface. Probes can be prepared using any convenient methodology, such as automated solid phase synthesis protocols, monoclonal antibody culture, isolation from serum, lipid synthesis, protein folding reactions, carbohydrate purification, recombinant protein technology and like, using such techniques as are known in the art. The probes are spotted on the support using any convenient methodology, including manual techniques, e.g. by micro pipette, ink jet, pins, etc., and automated protocols.

In one embodiment, an automated spotting device is utilized, e.g. Perkin Elmer BioChip Arrayer™. A number of contact and non-contact microarray printers are available and may be used to print the binding members on a substrate. For example, non-contact printers are available from Perkin Elmer (BioChip Arrayer™), Labcyte and IMTEK (TopSpot™). These devices utilize various approaches to non-contact spotting, including piezo electric dispension; touchless acoustic transfer; en bloc printing from multiple microchannels; and the like. Other approaches include ink jet-based printing and microfluidic platforms. Contact printers are commercially available from TeleChem International (ArrayIt™). Non-contact printers are of particular interest because they are more compatible with soft/flexible surfaces and they allow for a simpler control over spot size via multiple dispensing onto the same location. In one embodiment Non-contact printing is preferred for the production of high-specificity cellular microarrays. By utilizing a printer that does not physically contact the surface of substrate, no aberrations or deformities are introduced onto the substrate surface, thereby preventing uneven or aberrant cellular capture at the site of the spotted probe. Such printing methods find particular use with high specificity hydrogel substrates.

Printing methods of interest, including those utilizing acoustic or other touchless transfer, also provide benefits of avoiding clogging of the printer aperature, e.g. where probe solutions have high viscosity, concentration and/or tackiness. Touchless transfer printing also relieves the deadspace inherent to many systems, allowing the microzation of the probes themselves. The use of low shear forces, e.g. with acoustic transfer, also minimizes probe damage. To implement high-throughput printing, the use of print heads with multiple ports is preferred, and the capacity for flexible adjustment of spot size.

The total number of binding member spots on the substrate will vary depending on the number of different binding probes and conditions to be explored, as well as the number of control spots, calibrating spots and the like, as may be desired. Generally, the pattern present on the surface of the support will comprise at least about 2 distinct spots, usually at least about 10 distinct spots, and more usually at least about 100 distinct spots, where the number of spots can be as high as 50,000 or higher, but will usually not exceed about 10,000 distinct spots, and more usually will not exceed about 5,000 distinct spots. Each distinct probe composition may be present in duplicate or more (usually, at least 3 replicas) to provide an internal correlation of results. Also, for some tasks (such as stem cell fate manipulation and other cases, in which a group of cells tend to grow and occupy several spots) it is desirable to replicate blocks, each of several identical spots. In such cases replicate spots may be positioned in different neighboring spots to allow for estimation and compensation for potential cross talk effects (e.g. via soluble factors that are differentially secreted from cells on some of the spots). The spot will usually have an overall circular dimension and the diameter will range from about 10 to 5,000 µm, usually from about 100 to 1000 µm and more usually from about 200 to 700 µm. The binding member will be present in the solution at a concentration of from about 0.0025 µg/ml to about 50 µg/ml, and may be diluted in series to determine binding curves, etc.

By printing onto the surfaces of (preferably flat surfaced) multi-well plates, one can combine the advantages of the array approach with those of the multi well approach. Since the separation between tips in standard microarrayers is compatible with both a 384 well and 96 well plate, one can simultaneously print each load in several wells. Printing into wells can be done using both contact and non-contact technology, where the latter is also compatible with non-flat multi-well plates. The surface of the wells in the multi-well plate may be functionalized and/or coated so as to make them more compatible with specific cell-array applications. Other geometries, such as capillaries and blood collection tubes are also possible as substrates. Surface materials can also include nanotubes, modified or coated to allow binding of a capture probe. Surfaces which otherwise are not repellent of cells enough to adequately reduce background binding may also be used in association with a repellent coating, or an electric or magnetic field which weakly repulses cells from the array surface.

Signaling Probe.

The signaling probe may be used as an agent for specific cell binding, or may be provided in conjunction with a binding probe. Any molecule capable of eliciting a phenotypic change in a cell may be used as a signaling probe. Signaling probes may be the products of other cell types, (for example, expressed proteins associated with a disease, or secreted in a normal situation or during development), may be compounds associated with the ECM, may be compounds that simulate naturally occurring factors, may be fragments of cells, may be surface membrane proteins free of the membrane or as part of microsomes, etc.

Signaling probes may be used individually or in combination. Illustrative naturally occurring factors include cytokines, chemokines, differentiation factors, growth factors, soluble receptors, hormones, prostaglandins, steroids, etc., that may be isolated from natural sources or produced by recombinant technology or synthesis, compounds that mimic the action of other compounds or cell types, e.g. an antibody which acts like a factor or mimics a factor, such as synthetic drugs that act as ligands for target receptors. Where a family of related factors are referred to with a single designation, e.g. IL-1, VEGF, IFN, etc., in referring to the single description, any one or some or all of the members of the group are intended. Compounds are found among biomolecules including peptides, saccharides, fatty acids, steroids, purines, pyrimidines, oligonucleotides, polynucleotides, derivatives, structural analogs or combinations thereof.

Signaling probes can include cytokines, chemokines, and other factors, e.g. growth factors, such factors include GM-CSF, G-CSF, M-CSF, TGF, TNF-α, etc., extracellular matrix components, surface membrane proteins, such as integrins and adhesins, and other components that are expressed by the targeted cells or their surrounding milieu in vivo. Components may also include soluble or immobilized recombinant or purified receptors, or antibodies against receptors or ligand mimetics.

Included are pharmacologically active drugs, genetically active molecules, etc. Compounds of interest include chemotherapeutic agents, anti-inflammatory agents, hormones or hormone antagonists. Exemplary of compounds suitable as binding pair members for this invention are those described in The Pharmacological Basis of Therapeutics, Goodman and Gilman, McGraw-Hill, New York, N.Y., (1993) under the sections: Drug Therapy of Inflammation; Chemotherapy of Neoplastic Diseases; Drugs Used for Immunosuppression; Drugs Acting on Blood-Forming organs; Hormones and Hormone Antagonists; all incorporated herein by reference. Also included are toxins, and biological and chemical warfare agents, for example see Somani, S. M. (Ed.), "Chemical Warfare Agents," Academic Press, New York, 1992).

Cells.

Cell samples for use in the assays of the invention typically include biological samples and fluids that are suspected of containing T cells, or T cell progenitors, and may include lymph nodes, spleen, thymus, bone marrow, fetal liver, blood lymph, cerebrospinal fluid, synovial fluid, and the like, and derivatives therefrom.

The invention is suitable for use with any cell type, including primary cells, normal and transformed cell lines, transduced cells and cultured cells, which can be single cell types or cell lines; or combinations thereof. In assays, cultured cells may maintain the ability to respond to stimuli that elicit a response in their naturally occurring counterparts. Cultured cells may have gone through up to five passages or more, sometimes 10 passages or more. These may be derived from all sources, particularly mammalian, and with respect to species, e.g., human, simian, rodent, etc., although other sources of cells may be of interest in some instances.

In addition, cells that have been genetically altered, e.g. by transfection or transduction with recombinant genes or by antisense technology, to provide a gain or loss of genetic function, may be utilized with the invention. Methods for generating genetically modified cells are known in the art, see for example "Current Protocols in Molecular Biology", Ausubel et al., eds, John Wiley & Sons, New York, N.Y., 2000. The genetic alteration may be a knock-out, usually where homologous recombination results in a deletion that knocks out expression of a targeted gene; or a knock-in, where a genetic sequence not normally present in the cell is stably introduced.

A variety of methods may be used in the present invention to achieve a knock-out, including site-specific recombination, expression of anti-sense or dominant negative mutations, and the like. Knockouts have a partial or complete loss of function in one or both alleles of the endogenous gene in the case of gene targeting. Preferably expression of the targeted gene product is undetectable or insignificant in the cells being analyzed. This may be achieved by introduction of a disruption of the coding sequence, e.g. insertion of one or more stop codons, insertion of a DNA fragment, etc., deletion of coding sequence, substitution of stop codons for coding sequence, etc. In some cases the introduced sequences are ultimately deleted from the genome, leaving a net change to the native sequence.

Cell types that can find use in the subject invention include stem and progenitor cells, e.g. hematopoietic stem cells; hematopoietic cells such as Th1 T cells, Th2 T cells, Th0 T cells, cytotoxic T cells and genetically modified cells thereof. Hematopoietic cells may be associated with inflammatory processes, autoimmune diseases, etc.; and can also be associated with neoplasias, such as lymphomas or leukemias.

The cell sample may be pre-treated by freezing, fixing, labeling, pre-sorting, mixture with known or unknown cell types, and the like. Differential labeling can be used as a tool for proving detection of specific cell types and evaluating the detection limits. In addition, it provides an internal calibration for quantitative measurements. Cell populations can be labeled with different dyes, followed by their co-incubation onto the same array. Labels of interest include lipophilic tracers, e.g. DiO, DiI and DiD, which are incorporated into the cell membrane. Alternative labeling techniques include non-specific labeling of cell surface proteins (e.g. the Amersham FluoroLink technology), DNA/RNA incorporating dyes (e.g. the Molecular probes Syto dyes), membrane-permeate reactive tracers (e.g. Molecular Probes Thiol-Reactive CellTracker Probes), and other methods known in the field. Labels also include radiolabels, such as $^3$H or $^{125}$I, fluorescers, dyes, beads, chemilumninescers, colloidal particles, and the like. Suitable fluorescent dyes are known in the art, including fluorescein isothiocyanate (FITC); rhodamine and rhodamine derivatives; Texas Red; phycoerythrin; allophycocyanin; 6-carboxyfluorescein (6-FAM); 2',7'-dimethoxy-4',5'-dichloro-6-carboxyfluorescein (JOE); 6-carboxy-X-rhodamine (ROX); 6-carboxy-2',4',7',4,7-hexachlorofluorescein (HEX); 5-carboxyfluorescein (5-FAM); N,N,N',N'-tetramethyl-6-carboxyrhodamine (TAMRA); sulfonated rhodamine; Cy3; Cy5; etc.

Microenvironment.

The cellular microenvironment, or environment, encompasses cells, media, factors, time and temperature. Environments may also include drugs and other compounds, particular atmospheric conditions, pH, salt composition, minerals, etc. Culture of cells is typically performed in a sterile environment, for example, at 37° C. in an incubator containing a humidified 92-95% air/5-8% $CO_2$ atmosphere. Cell culture may be carried out in nutrient mixtures containing undefined biological fluids such a fetal calf serum, or media which is fully defined and serum free. A variety of culture media are known in the art and commercially available.

Phenotype.

Various cellular outputs may be assessed to determine the response of the cells to the input variable, including calcium flux, BrdU incorporation, expression of an endogenous or a transgene reporter, metabolic reporters, release of cellular products, cell motility, size, shape, viability and binding, etc. In some case (such as when cells are embedded in a 3D gel), even local pH levels or $O_2$ and $CO_2$ concentrations can be assayed. Generally the analysis provides for site specific determination, i.e. the cells that are localized at a spot are analyzed for phenotype in an individual or spot specific manner, which correlates with the spot to which the cells are localized.

The phenotype of the cell in response to a signaling probe or a microenvironment may be detected through changes in cell various aspects, usually through parameters that are quantifiable characteristics of cells. Characteristics may include cell morphology, growth, viability, expression of genes of interest, interaction with other cells, and include changes in quantifiable parameters, parameters that can be accurately measured.

A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. Parameters may provide a quantitative readout, in some instances a semi-quantitative or qualitative result. Readouts may include a single determined value, or may include mean, median value or the variance, etc. Variability is expected and a range of values for each of the set of test parameters will be obtained using standard statistical methods with a common statistical method used to provide single values.

Parameters of interest include detection of cytoplasmic, cell surface or secreted biomolecules, frequently biopolymers, e.g. polypeptides, polysaccharides, polynucleotides, lipids, etc. Cell surface and secreted molecules are a useful parameter type as these mediate cell communication and cell effector responses and can be readily assayed. In one embodiment, parameters include specific epitopes. Epitopes are frequently identified using specific monoclonal antibodies or receptor probes. In some cases the molecular entities comprising the epitope are from two or more substances and comprise a defined structure; examples include combinatorially determined epitopes associated with heterodimeric integrins. A parameter may be detection of a specifically modified protein or oligosaccharide.

A parameter may be defined by a specific monoclonal antibody or a ligand or receptor binding determinant. Parameters may include the presence of cell surface molecules such as CD antigens (CD1-CD247), cell adhesion molecules; secreted products such as lymphokines, chemokines, etc., including IL-2, IL-4, IL-6, growth factors, etc.

Profiling Methods

Passive Profiling.

In methods of passive profiling, a suspension of cells is allowed to bind to a array of binding complexes. The suspension is applied to the substrate without a cover or under a coverslip, or into a fixed volume of "incubation" or a "perfusion" chamber. The incubation time should be sufficient for cells to bind the complexes. Generally, from about 4 minutes to 1 hr is sufficient, usually 20 minutes sufficing. Various methods may by used in application of the cells, including agitation (including ultrasonic agitation), shaking, tilting, flow of cells across substrate (manually, or with peristaltic or microfluidic pumps, evaporation-induced etc'), mixing using surface sound waves and the like, mixing of bead-isolated cells using magnetic stirrers, variations in temperature, time, concentration of cells applied, number of cells applied, composition of sample fluid, e.g. blood, lymph, media, and the like. The array may be washed one or more times after application of the cells.

While many assays are performed with live cells, passive assays may also be performed with fixed cells. Cells fixed with various concentrations of reagents such as PFA, glutaraldehyde, methanol, acetic acid, etc. can be used alone, or in comparison with non-fixed cells.

After incubation, the insoluble support is generally washed to remove non-specifically bound cells in any medium that maintains the viability of the cells and the specificity of binding, e.g. RPMI, DMEM, Iscove's medium, PBS (with or without $Ca^{++}$ and $Mg^{++}$, depending on the type of probe being used), etc. The number of washes should be determined experimentally for each application and cell type by observing the degree of non-specific binding following each wash round. In many instances, there is no non-specific binding, but washes may still be required to completely remove freely floating cells. Usually from one to six washes are employed, with sufficient volume to thoroughly wash non-specifically bound cells present in the sample.

Passive profiles can be absolute or differential. In an absolute profile, a single cell type is added to the array, and the number of bound cells detected. Occupied spots denote the presence of the corresponding cell surface marker to the binding probe. Over a range of cell and probe concentrations, the higher the expression level, the higher the number of captured cells. However, absolute profiles can be susceptible to spot- and slide-related variations.

A differential profile is a competitive assay, where two or more cell types/populations are pre-labeled with different labels, combined and applied to a single slide, where they compete for binding to probe molecules. Following washout, the slide can be scanned and scored for the relative number of label present for each of the cell types.

In order to detect the presence of bound cells from each type, a variety of methods may be used. In an absolute assay, the cells need not be labeled at all, or may be labeled with a detectable label, and the amount of bound label directly measured. In a differential assay, labeled cells may be mixed with differentially labeled, or unlabeled cells and the readout could be based either on the relative number of pixels with a given label (or no label, respectively) or the relative number of cells with a given label (or no label, respectively). In yet another embodiment, the cells themselves are not labeled, but cell-type-specific second stage labeled reagents are added in order to quantitate the relative number of cells from each type, or to phenotype the cells. In some instances the cells will not be quantitatively measured, but will be observed for such phenotypic variation as morphology, adherence, etc.

Cell arrays can be scanned to detect binding of the cells, e.g. by using a simple light microscopy, scanning laser microscope, by fluorimetry, a modified ELISA plate reader, etc. For example, a scanning laser microscope may perform a separate scan, using the appropriate excitation line, for each of the fluorophores used. The digital images generated from the scan are then combined for subsequent analysis. For any particular array element, the ratio of the fluorescent signal with one label is compared to the fluorescent signal from the other label cells, and the relative abundance determined.

Active profiling (AP) and functional binding assays (FBA).

In an AP assay, the presence of a given marker is indirectly detected by assaying the fingerprints of its activation (e.g. detection of a functional, antigen-specific TCR via the detection of spot-specific induction of calcium flux, or spot-specific changes in other relevant reporters). An FBA is a specific type of AP, in which a signaling probe actively induces cells to bind to a co-spotted MHC complex. In this case, the induction of detectable TCR is assayed by the enhancement of cell binding. Alternatively, a stimulation of the TCR by, say low dosage of immobilized MHC-peptide complex may lead to cell binding to a second agent (e.g. ICAM) that is co-spotted with the MHC-peptide. FBA can be used to screen for cues capable of enhancing cell binding, for example in exploring the dynamics of T cell education.

Similarly to passive profiling, functional binding assays can be performed in an absolute or a differential manner. However, unlike passive profiling, the MHC complex in a functional binding assay is either co-spotted with an additional, stimulating cue or juxtaposed to a stimulating cue (e.g. the latter will be present on an adjacent spot). Other examples of active profiling, which do not necessarily involve the induction or enhancement of binding, include any assayable change in one or more cell parameters on spots that contain a given signaling probe, vs. those spots that that do not contain that signaling probe.

A signaling probe can be detected for its ability to enhance the binding of cells to a particular binding probe, and/or for other changes in phenotype. For example, a signaling probe may induce expression of a cell surface marker. While the starting cell population will be unable to bind to the counterpart binding probe, cells responding to the signaling probe will bind.

Results of active profiling assays can be read out as the absolute or differential scores. Readouts of interest include calcium flux following stimulation, changes in expression of markers including reporter genes, and cell surface receptors, changes in BrdU incorporation corresponding to changes in proliferation rates, etc.

One embodiment of active profiling assays is screening for activity of drug candidates, by printing with or without a capture molecule (e.g. MHC-peptide complex). Candidate agents include agents that act inside the cells, and on the cell surface, as described above. To improve the interactions with cells, candidate agents may be printed onto a film-coated slide or in a 3D gel. Sustained release of an agent can be achieved by printing a mixture that releases active agents from a polymer gel or by slow hydrolysis of a linker, through which the active agent is connected to the surface.

In some embodiments, the candidate agent is bound to a polypeptide carrier, which may be a binding probe, a receptor that specifically interacts with the agent, and the like. For example, steroid compounds may be presented in conjunction with their appropriate carrier protein.

Included in the candidate agents that may be screened are arrays of peptide libraries. Peptides, which may provide signaling and/or binding functions, are tested by exposing cells to an arrayed library, which may be random sequences, shuffled sequences, known sequences that are randomly mutated, etc. Of particular interest are MHC-restricted peptides that may be co-spotted with a capture probe and subsequently picked up by captured cells, including antigen presenting cells, which can present the peptide to T cells. In this way, large antigen libraries can be displayed by immobilized cells that were pulsed with a spot-dependent antigen. In another important embodiment, a library of putative MHC-restricted peptide targets is created by mutating the variable regions of the peptides. These peptides can then be loaded into MHC monomer, MHC DimerX, MHC tetramer or any other MHC construct and spotted individually and/or as pooled MHC-peptides (pooling can be performed either prior or following the incorporation into the MHC construct). Reactive side chains may be capped prior to the immobilization and uncapped just before applying the cells. The peptides can be bound to the substrate directly, or via a linker attached to one end, bound to a carrier protein, etc. The peptides may be synthesized directly onto the substrate, (see, for example, U.S. Pat. No. 5,143,854).

Cell-cell Interaction Assays.

The ability to specifically capture any type of cells onto defined locations and to form patterned surfaces with feature sizes on the order of one or few cell diameters, can be used to juxtapose two or more different cell types, and study their mutual interactions. Different cells can be immobilized within the same spots by printing a common binding probe or co-printing of two or more cell-type specific binding probes. Alternatively the cells can be immobilized separate, nearby spots using cell-type-specific binding probes. In another embodiment, antigen-specific T cells can be captured by the corresponding MHC-antigen complex (or by another suitable probe) and subsequently used as cellular probes to specifically capture (either labeled or unlabeled) target cells that are suspended (separately or in mixtures) on top of the already immobilized T cells. Target cells that are captured by the T cells would remain on the slide following washout of unbound cells and the interaction between the two cell types can be studied with conventional methods (e.g. studying killing interactions using Chromium-51 or with cell viability kits that are available form Molecular Probes). If cell-type-specific capture molecules are not known, the cells can be screened in an absolute or differential profiling experiment to determine suitable binding partners.

In order to obtain juxtaposition of distinct cell types on nearby spots, those populations may need to be segregated, such that each spot will include only one cell type. This can be achieved by performing an initial screen of cell-type-specific binding partners to screen for binding probes that segregate these populations (as judged by morphology, marker profile, or any other suitable method). For example, one can segregate T cells; B cells; antigen presenting cell including dendritic cells; thymic epithelial cells; etc. by exposing the cells to an antibody array that includes a set of antibodies specific for one subset of immune cells and another set for MHC-antigen complexes. These binding complexes and probes are then printed at the desired pattern on another array, and thus used for simultaneous segregation and juxtaposition of, for example, T helper cells and B cells; or immature thymocytes and thymic epithelial cells. Subsequently, the cells can be co-cultured and the juxtaposed cells can be compared to nonjuxtaposed cells that were captured and cultured on the same slide. An alternative approach can print different cell types onto nearby spots using a non-contact printing technology.

Following immobilization, the cells may be maintained in culture, either on the array substrate, or after removal of the captured cell population. Cells may be removed by mechanical methods, e.g. pipette, or by release, e.g. by cleavage of the binding complex. Alternatively, bound cells can be transferred to a gel, e.g. an ECM gel (or any other suitable substance that can serve as a "sink" for the cells), by polymerizing or layering the gel directly onto the cells. The latter can then migrate to the gel and form cell clusters, which still preserve the array's coordinates information. Transferred cells can be further maintained and/or expanded inside the gel and/or dissected out by cutting the relevant sections of the gel and recovering the cells from those sections using standard methods. Cells can be released from the array in a variety of ways, e.g. by pipetting off the substrate, for quantitation, further phenotypic characterization, and the like.

In addition to the formats described above, the assays of the invention may use three dimensional gels, e.g. an ECM gel such as "VITROGEN 100" collagen gel, (Cohesion Technologies, Inc). The probes may be printed on the gel within which cells are pre-embedded; signaling probes may be printed together with binding probes, or followed by exposure to the cells and washout of non-attached cells. Alternatively the cells may be printed together with signaling probes (provided that the gel is properly hydrated).

Printing onto gels can be performed with a non-contact micro-dispensing system, e.g. Perkin Elmer "Biochip Arrayer" (BCA). Such systems utilize a non-violent dispensing mechanism (contraction of piezzo-electric sleeve). Tips with a relatively wide open, e.g. at least about 30 µm, that provide for drops of a volume of greater than 20 nl. For example, the volume of each drop dispensed with the BCA (0.25-0.5 nl), allow for cell deposition along with signaling probes of interest. In addition, probes and cells to be locally added at later stages (either by using a positioning camera or by accurately re-positioning the arrays for additional print runs.

The three dimensional array and some film coated slides as substrates for printing allows for diffusion of (passive and/or signaling) probes, where the effect of a gradient on a cell can be analyzed. The printed probes diffuse and form potentially important continuous gradients.

Cells can be applied and washed away from the surface of an un-printed "VITROGEN" collagen gel, or can be cultured within it by mixing them with the neutralized liquid phase of the gel prior to gelation (fibrillogenesis), initiating gelation by raising the temperature from 4° C. to 37° C., and culturing the (solid) gel in a standard medium.

Data Acquisition.

In implementations of cellular microarrays where high throughput molecular and functional profiling is desired, an appropriate method of high throughput data acquisition is required for enablement. Cell microarrays can be scanned to detect binding of the cells, e.g. by using a simple light microscopy, scanning laser microscope, by fluorimetry, a modified ELISA plate reader, etc. For example, a scanning laser microscope may perform a separate scan, using the appropriate excitation line, for each of the fluorophores used. The digital images generated from the scan are then combined for subsequent analysis. For any particular array element, the ratio of the fluorescent signal with one label is compared to the fluorescent signal from the other label DNA, and the relative abundance determined.

Generally, optical scanning is preferred, using an automated microscope and a motorized stage. Robotic loading of slides onto the microscopy platform allows a further increase in throughput. Cellular microarrays can be marked with predetermined geographic locations that allows identification of array start and stop points. This can be achieved using a spot containing a visible dye, a fluorescent dye or marker or an expected cell binding pattern at a particular location. In the simplest implementation, a single spot is thus labeled, marking a position on the array grid, such as in one corner. In more sophisticated implementations, all corners, or pre-determined patterns of markers are printed. Once these markers are identified, automated data acquisition in all involved channels may be performed (for example, but not limited to brightfield/phase contrast/DIC/Color, FITC, CY5, CY3, DAPI, PI, UV, etc.). Automated analysis is also of interest, allowing automated counting of cells binding to each spot, cell morphology, fluorescence intensity, etc. Automated analysis may include comparison with an established database, clustering by phenotype, etc.

The agents utilized in the methods of the invention may be provided in a kit, which kit may further include instructions for use. Such a kit may comprise a printed array. The kit may further comprise cells, labeling reagents, assay reagents for monitoring changes in cell phenotype, singling probes, and the like.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Experimental

Methods

Preparation of tetramer arrays: PE-labeled MHC-peptide tetramers were synthesized for the MHC class I (H-2k$^b$) murine antigen ovalbumin (OVA) and MHC class II (I-E$^k$) murine antigen moth cytochrome C (MCC) as described by Altman et al., supra. and validated by FACS using OT-1 OVA-specific T cell receptor (TCR) transgenic mice and 5CC7 MCC-specific TCR transgenic mice, respectively. The following MHC tetramers and antibodies were prepared in a v-shaped 384-well plate (Genetix, cat# x6004) with approximately 12µl per well (about twice the minimal volume): (i) A 2-fold dilution series of the Ova tetramer (1 to 1:16x, with final 1x concentration being 0.17 mg/ml), (ii) class I (HLA-A2) human melanoma antigen gp100 (at 0.52 mg/ml), (iii) MCC tetramer (0.42 mg/ml), (iv) anti-mouse CD3 monoclonal antibody at 0.5 mg/ml, (v) anti-mouse CD28 monoclonal antibody at 0.5 mg/ml and (vi) a 1:1 mixture of anti-mouse CD3 and anti-mouse CD28 (each at a final concentration of 0.25 mg/ml).

In order to overcome the problem of low binding affinity to the MHC-peptides the concentration and activity of the spotted complexes was optimized. In particular, a substrate was selected that is inert for cell binding while at the same time exhibits high capacity for protein deposition with high fidelity (say, as compared with a derivatized slide). An arrayer capable of dispensing multiple samples on each spot with minimum film disruption or degradation was used. Tests were performed with supplementation of the spotting solution with stability enhancing agents.

The data presented here was obtained using commercially available slides coated with a 12 by 40 (or 12 by 12) mm film of polyacrylamide (Perkin Elmer HydroGel slide) and a non-contact piezzo-electric arrayer (Perkin Elmer BCA). The poly-acrylamide film was found to allow stable MHC-peptide spots, and eliminate non-specific binding to the substrate while still enabling detectable binding of antigen-specific T cells to the MHC-peptide complexes. The BCA arrayer employs 4 independent tips to flexibly aspirate and dispense up to 4 samples per load. It enables multiple dispensing of the sample onto the same spot, thereby allowing controlled increase of both the spot size and the amount of material deposited. Using this feature, ~4.5 nl of each sample were dispensed on each spot (10 drops of ~0.45 nl each).

The resulting spot size (with ten, 0.45 nl drops of proteins dispensed at 0.5 to 1 µg/µl on a Hydrogel slide) is about 400 µm in diameter and each of these 10 drop spots can accommodate up to about 1600 cells of 10 µm in diameter. The combination of large spots on an inert substrate allows confident detection of as low as about 5 to 10 cells bound to the spot. This corresponds to a dynamic range of about 300 fold, which can be further increased by increasing the spot size (i.e. dispensing more drops on each spot).

The addition of glycerol or Tween 20 to the spotted MHC-peptide solutions can improve the binding, particularly at concentrations of tetramer lower than 0.8 mg/ml. Therefore, each of the constructs was supplemented with glycerol to a final concentration of 2%.

Figure 1A:
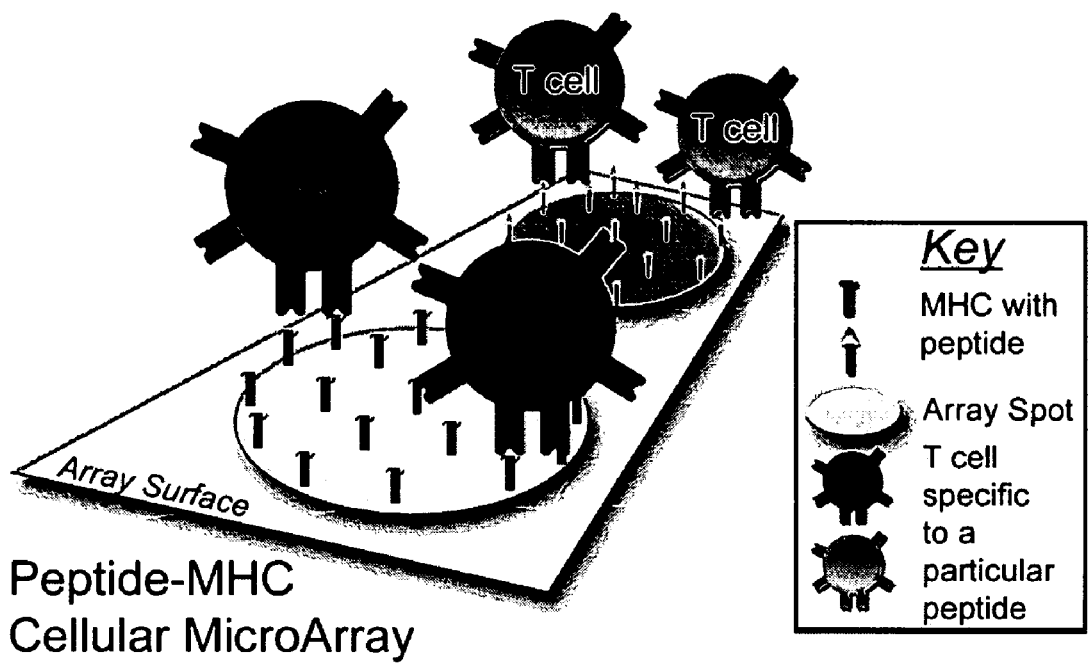
FIG. 1A-B. A cellular microarray. A. A schematic diagram illustrating T cell binding to its cognate peptide-MHC spot via TCR-peptide-MHC interactions (not drawn to scale). B. Cells immobilized on the cellular microarray are immediately visible to inspection. When cell coverage exceeds ~20% confluency, the cluster becomes visible to the naked eye. Shown are cell clusters bound to several triplicate spots of either peptide-MHC complexes or antibodies. The image was taken using a consumer digital camera. The arrows and legends indicate the locations and identities of each of the printed triplicates. Spot diameter and inter-spot distance are about 400 μm and 700 μm, respectively. Scale bar is 1.4 mm in length.
Figure 1B:
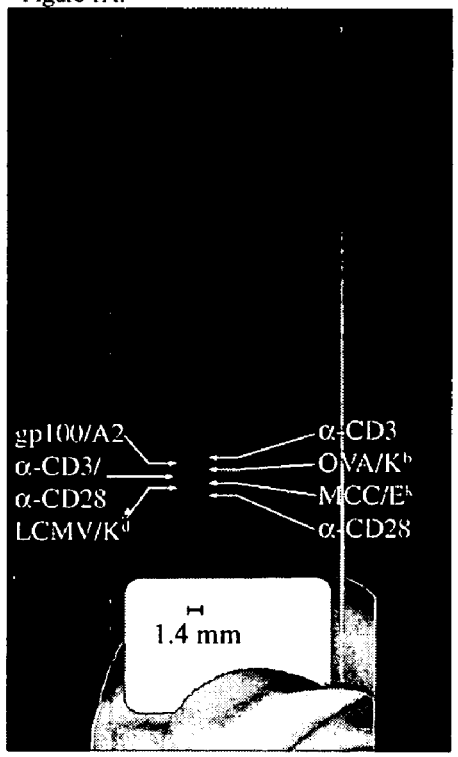

The Hydrogel slides were preprocessed for printing according to the manufacturer instructions. In order to allow for more than one assay on each slide, each of the samples was dispensed in two groups (or blocks) of 3 spots each, with an inter-spot distance (in both X and Y directions) of 700 µm (about 300 µm above the minimum required for complete separation between neighboring spots) and an inter-group distance of 5 mm. Each block is actually a 3 by 6 array printed with the same tip (see FIG. 1A for an example of one such block). Each slide was printed with two replicates of four blocks, each comprising 3 (relatively large) spots per any given sample.

The results presented here are based only on two of the four blocks. To simplify the identification of each spot within the blocks, the first column in each block comprised of 3, positive-control, α-CD3 spots, which was capable of immobilizing all cell types that are relevant to this example. In addition, the lining of each block was marked (either outside the film region or on the back side of the slide) right after the printing process, at which point, the spot columns are still visible to the naked eye). Finally, since all tetramer spots were PE-labeled, they were used for fluorescence-based position marking. Thus, the phycoetherin (PE) labeling was used (together with the print layout) to identify each spot, determine its border, evaluate its size, and examine differences in spot size over time.

Following the print run, the arrayed proteins were immobilized within the gel substrate by incubating the slides for 24 hours at 4° C. in a humid chamber. After the incubation, the slides were placed in a dry slide box, sealed with a tape and stored at 4° C. until used. Stored slides were used for 5 months without an observed reduction in activity or diffusion of the spotted constructs (lack of diffusion was determined by examining the diameter of the PE-labeled MHC tetramer spots as viewed by fluorescence microscopy).

Preparation of DimerX Arrays.

To test the feasibility of generating arrays with large libraries of MHC-restricted peptides, DimerX-peptide arrays were prepared and tested. The DimerX construct is supplied with a pre-loaded peptide, which can be swapped with other, MHC-restricted peptides, thereby creating a library of MHC-peptides. DimerX was loaded with the OVA peptide according to the manufacturer's protocol and both the DimerX-OVA and its unswapped version were printed in a similar fashion to the MHC tetramers.

Preparation of Cells.

OT-1 and 5CC7 transgenic mice were sacrificed and lymphocytes were harvested from inguinal and axillary lymph nodes on day 0. 1 μM OVA and MCC peptides were added to the respective single-cell suspensions. Active OT-1 (CD8+) and 5CC7(CD4+) lymphocytes were selected on day 10 (OT1) or 6 (5CC7) by binding to plastic petri dishes. Alternatively, OT1 transgenic mice were either non-immunized or immunized twice (with one week separation between vaccination events) and sacrificed after the $2^{nd}$ vaccination. Ot1 lymphocytes were then harvested and used on day 0. As syngeneic controls, B10A or C57bl/6 mice were sacrificed and single cell splenocyte suspensions were subjected to a Ficoll gradient prior to being utilized.

Pre-Labeling of Cells.

Differential profiling of cells is a key concept enabling quantitative comparative analysis of cells, in general, and of immune responses, in particular. In addition, it can be used as a tool for proving detection of specific cell types (not just specific markers) and evaluating the detection limits. This concept is based on labeling distinct cell populations with different dyes, followed by their co-incubation onto the same array. Here we describe one efficient, multi-color labeling scheme. This method utilizes DiO, DiI and DiD lipophilic tracers (Molecular Probes, Vybrant Multi-Color Cell-Labeling Kit), which are incorporated into the cell membrane.

Cells were suspended in serum-free medium (RPMI+PSG) at $10^6$ cells/ml. Labeling reactions were preformed by adding 3 μl of labeling solution per 1 ml of suspension and incubating the mixture for 5' at 37° C. Cells were then washed 3 times with complete growth medium (RPMI+10% FCS+PSG+β-mercaptoethanol+non-essential amino acids) by spinning at 1200 rpm for 5'. Following the $3^{rd}$ spin, the cells were re-suspended in growth medium and transferred into the incubator for a 15-30' recovery. This method does not affect the specificity of cell capture on the array. In addition, it is very simple and effective, yielding very good staining results without any observable bleed-through (e.g. when DIO and DID are used for differential labeling).

Exposure of Cells to the Array.

Unlabeled and/or pre-labeled cells were re-suspended in either RPMI+1% BSA or "Imaging medium" (deficient RPMI+5% FCS+PSG+β-mercapto-ethanol+non-essential amino acids) at concentrations that range between $10^5$ to $10^9$ cells/ml. In some experiments, the suspended cells or mixtures were directly applied to the entire array (i.e. to all the printed blocks). In most cases, however, one or more blocks were first separated by (thin) sticky silicon or rubber stripes that were attached to unprinted regions between blocks. The stripes were cut from perfusion chambers (GRACE BIO-LABS, CoverWells) or from seals of LabTek chambers. Once attached to the gel surface, these stripes act as barriers that split the array into separate regions, thereby allowing different assays to take place on the same slide. Suspended cells were added to the restricted portions of the array by gentle layering in volumes of 20 to 50 μl. The array was then either incubated at 37° C. or 20° C. for ten to 20 minutes. Longer incubation periods as well as occasional sample reloading (e.g. every 5 minutes for 30 minutes total) were also tested. Overnight incubation at 4° C. was found to improve the binding to MHC-peptide complexes and may be required for the detection of rare populations of cells (with or without a mixing mechanism). In contrast, binding to antibody spots is better at room temperature or 37° C. In order to optimize binding conditions for those arrays that contain both antibodies and MHC-peptides, we've successfully tested a modified protocol with initial 5 to 10 minutes incubation at 37° C. (to allow for an efficient binding to the antibody spots), followed by overnight incubation at 4° C.

Demonstrations of cell sorting and detection of a rare cell population can be performed with two or more differentially pre-labeled cell populations that are mixed at various ratios. For example, to demonstrate spot-dependent segregation of $CD4^+$ and/or $CD8^+$ cells from a $CD4^+CD8^+$ mixture, each population was first labeled separately with a different lipophilic tracer, mixed at a 1:1 ratio and applied together to the array. Similarly, to prove detection of rare cells, pre-labeled cell populations were mixed at highly uneven ratios (e.g. 1:100 of $OVA^+CD8^+$ to PBMCs). An efficient detection of a rare cell population typically requires relatively high cell densities of the total sample to enable the collection of a sufficient number of target cells on the corresponding spots. Efficient detections of 1% 5CC7 or 0.1 to 1% of OT1 target cells were demonstrated using total and target cell concentrations on the order of $10^8$ and $10^6$ cells/ml, respectively (shown in FIGS. 6 and 7). Significantly higher cell concentrations (say, total cell concentration of at least $10^9$ cell/ml), which can be easily obtained, would push the detection limit even further by increasing the number of antigen-specific cells that encounter the appropriate spot region. Effective mixing and/or sample flowing is expected to do the same.

Following the initial incubation on the array, the slide was dipped and moved back and forth in a large volume (~350 ml) of RPMI to remove unattached and/or weakly bound cells. In some cases cells were washed by several cycles of RPMI reloading onto the printed regions.

Assaying Binding Results.

Binding of cells to the array was viewed with standard and/or fluorescent microscopy (depending on the exact type of experiment), by either a manual or an automated scan and acquisition of images from the spotted regions. Bound cells in an entire spot are easily identified in 10× images and can be manually and/or automatically counted. In some cases, cell binding and/or activation and/or interactions was followed in time using an automated time-lapse video system, comprising a Zeiss Axiovert-100TV microscope (with a 10× objective) fitted with a high-speed piezzo electric z-motor (Physik Instruments), Princeton Instruments liquid cooled CCD Interline camera (Roper Scientific), and dual excitation and emission filter wheels (Sutter Instruments). A DIC image, and/or FITC (for DiO), and/or Cy3 (DiI), and/or Cy5 (DiD) images were collected every 15-30 seconds for up to one hour. Microscope control, acquisition of data and image analysis was performed using Metamorph (Universal Imaging).

Results

Demonstration of Specific Binding and Sorting With MHC-peptide Cell Arrays.

Figure 2:
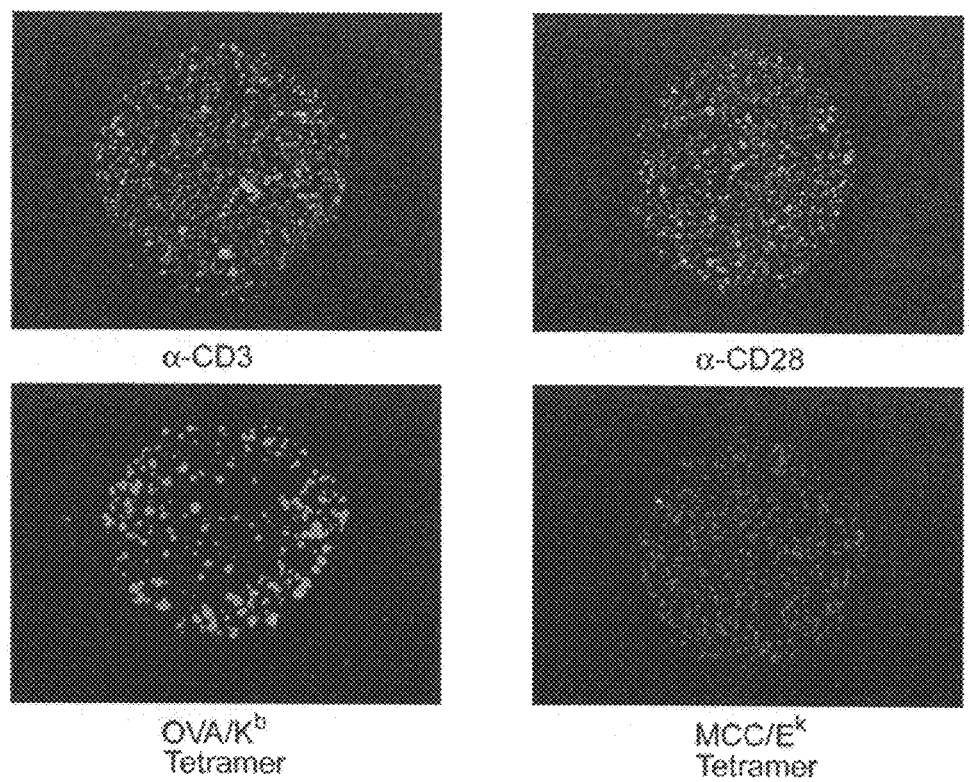
FIG. 2. Specificity of lymphocyte immobilization by peptide-MHC arrays. 6×10⁵ pre-labeled, OVA-specific OT-1 (green) and MCC-specific 5c.c7 (red) lymphocytes were mixed at a 1:1 ratio and added to the pre-printed peptide-MHC array. While anti-CD3 and anti-CD28 monoclonal antibody spots (left and right top panels) immobilize both lymphocyte populations, the OVA and MCC tetramers (left and right bottom panels) capture only the OVA-specific and MCC-specific cells, respectively. Cells were labeled with DiO and DiD lipophilic tracers that incorporate into the cell membrane and do not affect the specificity of cell capture.

Day 7 active OT-1 (CD8+) and 5CC7 (CD4+) lymphocytes were labeled with DiO (green) or DiD (red) lipophilic tracer respectively, prior to mixing in a 1:1 ratio. $6\times10^5$ lymphocytes were layered onto the array and incubated at 20° C. for 10 minutes. The array was then washed twice in RPMI prior to visualization of immobilized spots by fluorescence microscopy. Both OT-1 (green) and 5CC7 (red) lymphocytes bind (with different affinities) to α-CD3, α-CD28 and α-CD3/α-CD28 spots (FIG. 2). By contrast, none of the OT-1 cells were found on the MCC/IE$^k$ tetramer spots and likewise, none of the 5CC7 cells were captured on the OVA/K$^b$ tetramers. Thus the specificity was demonstrated by the complete sorting of OT-1 cells on the OVA/K$^b$ tetramer spots and 5CC7 cells on the MCC/IE$^k$ tetramer.

Specific cell binding to the array can be observed even without washing of unbound cells. FIG. 12 demonstrates antigen-specific spot formation during 14' of incubation at 37° C. Here, a small volume of mouse CD8$^+$ lymphocyte suspension was applied to an array containing MHC-OVA and MHC-LCMV tetramer spots. The spot regions were visualized in time lapse as the cells settled down on the slide and thereafter. Cells that reached the MHC-OVA spot were immobilized whereas unbound cells around the spot kept drifting away by evaporation-induced flow. The flow can enhance cell capture by effectively increasing the cross section for cell capture.

The ability to detect antigen-specific naive and memory T cells was tested. T cells from OT1 transgenic mice that were freshly vaccinated, unvaccinated, and vaccinated 2 months prior to harvesting were separately applied directly to the array without prior culturing, expansion or activation. Specific binding of the OT1 cells from all three mice to the OVA tetramer shows that the MHC array is sensitive enough to detect memory and even naïve T cells.

Usage of re-loadable MHC-peptide constructs: A method for generating arbitrary libraries. To explore the possibility of creating general libraries of MHC-bound peptides, the binding of OT1 cells to DimerX-OVA spots was tested. DimerX constructs are supplied with a default peptide that can be replaced with an arbitrary peptide. FIG. 3 shows OT1 cells that bind to α-CD3, and DimerX-OVA spots, but not to the DimerX-control spot. DimerX as well as tetramer constructs were further tested for the ability to specifically detect cancer antigens in human samples (FIG. 4). Both heteroclytic and naive versions of gp100 and MART1 melanoma antigens were loaded into separate DimerX/A2 constructs. These constructs along with tetramers complexed with the same peptides (commercially available from Beckman Coulter) and several anti-human antibodies, including an antibody against the relevant tissue type (i.e. α-HLA A2) were then printed on a HydroGel slide. gp100/g209-specific and MART1-specific tumor infiltrating cells (TILs) were FACS-sorted from melanoma patients, re-stimulated in vitro with peptide-pulsed APCs, (JY cells), PHA and 50 µ/ml IL-2, and frozen in aliquots. One aliquot of each was thawed and applied (separately) to duplicate arrays on the same slide. The cells were incubated on the arrays for 30' at 37° C. and non-attached cells were subsequently washed with RPMI. The resulting binding pattern reveals exclusive binding of the gp100/g209-specific cells to both the DimerX and tetramer gp100/g209 constructs (1$^{st}$ and 3$^{rd}$ rows from the top). Similarly, the MART1-specific cells only bind the MART1 tetramer and DimerX constructs (2$^{nd}$ and 4$^{th}$ rows from the top). Taken together, these results demonstrate: (i) identification of two melanoma-specific CTLs from human tumors, (ii) effective capture (confluent cell clusters) by constructs with supposedly lower affinity to the TCR (as compared with viral antigens), (iii) Capture via wild type TCRs (as compared with cells from transgenic mice), (iv) DimerX-mediated capture that is at least as effective as the corresponding tetramer-mediated capture, (v) successful usage of heteroclytic constructs, (vi) usage of frozen cell aliquots, and (vii) a consistent tissue typing result (via the α-HLA/A2 antibody) obtain with the same platform.

To evaluate the lower limit of the amount of tetramer required for binding as well as to examine the relation between tetramer concentration and the number of captured cells, we have printed an OVA/k$^b$ tetramer dilution series, and probed it with OVA-specific OT1 cells (FIG. 5A). To avoid saturation of the spot, the concentration of the OT1 suspension was set at $2.5\times10^6$ cell/ml ($10^5$ cells in 40 µl). Under these conditions the number of captured OT1s is found to be linearly dependent on the amount of tetramer deposited, with a binding threshold of approximately 0.05 ng/spot, emphasizing the low tetramer dosage required for binding (note that this threshold is cell- and MHC-peptide-dependent). The lack of background adherence between spots or on irrelevant MHC-peptide spots enables us to attribute the binding of as low as a few cells to TCR-MHC-peptide recognition. The linear relation extending all the way to the highest tetramer dosage FIG. 5B) indicates the possibility of further increasing the number of bound cells by increasing the amount of deposited tetramers. Indeed, increasing the amount of tetramer deposited to 1.3 ng/spot, leads to a significant increase in binding efficiency and the number of cell captured on an appropriate tetramer spot can be as high as obtained with a monoclonal antibody spot.

A titration of the MHC-peptide concentration is used for selection/sorting of antigen-specific cell populations based on the level of expression and/or the strength of the interaction with the corresponding TCR and/or the affinity of its interaction with the spotted MHC-peptide complexes. In the example shown in FIG. 5A, the cells that bind to more dilute MHC-peptide spots may express higher TCR levels and/or exhibit stronger TCR-MHC-peptide interactions. Also, by repeating the same experiment using different cell concentrations, it is possible to construct a scaling curve. The latter is used to translate differences in the number of captured cells to differences in the abundance of antigen-specific cells whose strength of interaction with the MHC-peptide spots is above the threshold required for binding.

Figure 6:
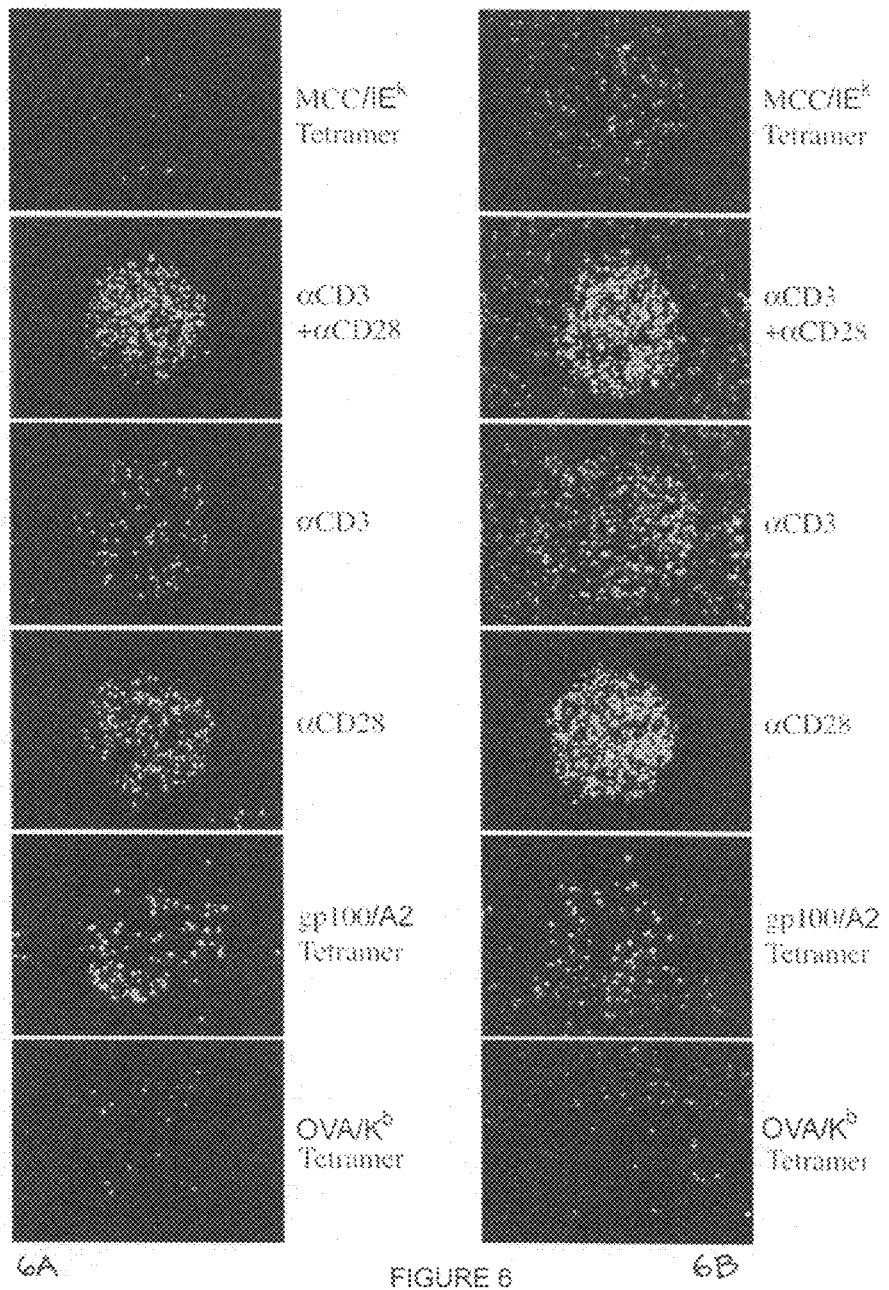

The feasibility of detecting a rare cell population (e.g. for diagnosis purposes) was demonstrated for class II MHC with DID-labeled 5CC7 MCC-specific lymphocytes diluted to 1% in syngeneic, DIO-labeled B10A splenocytes (FIG. 6B) and for class I MHC with DID-labeled OT1 OVA-specific cells diluted to 1 and 0.1% in DIO-labeled B6 lymph node cells that were depleted of monocytes (FIG. 7). $3.5\times10^4$ labeled 5CC7 lymphocytes were mixed with $3.6\times10^6$ B10A splenocytes prior to layering onto the pre-printed array. The cells were incubated at 37° C. for 12 minutes and the array was then washed in RPMI prior to visualization of cell binding by eye and examination of immobilized cell identities by fluorescence microscopy (FIG. 6). Despite the low population of 5CC7 lymphocytes in the cell mixture, specific adherence to the MCC MHC-peptide spot was observed. Almost all the cells that bind the MCC spots were indeed found to be 5CC7 cells (FIG. 6B). In addition, in a control experiment without the 5CC7 cells (FIG. 6A), very few splenocytes adhered to the MCC spots, as well as to other MHC-peptide spots, and most prominently to the cross-species human HLA-A2 gp100 MHC-peptide spot. This cross binding points at another important application for the array, namely the identification of cell types responsible for alloreactivity and/or xenoreactivity by counter staining with antibodies against known subtypes (e.g. α-CD94 for natural killer cells, CD19 for B cells, and CD11b for monocytes). To demonstrate detection of rare CTLs, DiD-labeled OT1 cells were diluted 1:100 (FIG. 7, top panels) and 1:1000 (bottom panels) in DiO-labeled, monocyte-depleted, B6 mouse lymph node cells and co-incubated onto different tetramer and antibody spots. Monocyte depletion was achieved by negative selection with α-CD11b (Mac1) beads. Following cell selection and differential labeling, $2.7 \times 10^4$ (top panels) and $4.41 \times 10^3$ (bottom panels) of OT1 cells were mixed with $2.7 \times 10^6$ and $4.41 \times 10^6$ of Mac1-depleted lymph node cells, respectively. The different dilutions were applied to identical, but separated, regions (of a single slide), each printed with $K^b$/OVA tetramers, $K^b$/LCMV control tetramers and three different antibody spots (α-mouse CD8, α-mouse CD4, and α-mouse CD28). Following 10' incubation at 37° C., the cells were washed in RPMI and the slide was scanned. The highly preferential and specific binding of OT1 cells to the OVA tetramer (on both top and bottom panels), together with the absence of OT1 binding to the LCMV tetramer, demonstrate the feasibility of detecting as low as 0.1% of antigen-specific T cells. Further enrichment via negative and/or positive selection using common markers would push the 0.1% limit further down.

Diagnosis of a weak immune response to a viral antigen (FIG. 8) on MHC-peptide array was demonstrated by the detection of OVA-specific T cells from a B6 wild type mouse that was vaccinated with Ovalbumin. C57BI/6 mice were vaccinated (day 0 and 7) with either 200 µg of Ovalbumin with Freund's Adjuvant or mock (phosphate buffered saline and Freund's Adjuvant). Nearest lymph node's cells were harvested on day 11 and CTLs were isolated using CD8-beads. CTLs from both the vaccinated and control (mock-vaccinated) mice were split and used for flow cytometry and MHC-array analysis. $2*10^6$ and $3.2*10^6$ cells from the OVA- and mock-vaccinated mice, respectively, were layered on duplicate arrays (on the same slide) printed with OVA/H2k$^b$ tetramer, LCMV/H2k$^b$ (control) tetramer and various antibodies. The cells were then incubated for 30' at room temperature and freely floating cells were subsequently washed with RPMI. FACS analysis revealed that the control mouse did not have detectable, OVA-specific CTL response, whereas a small fraction (about 0.22%) of the CTLs from the vaccinated mouse was found to be OVA-specific. Consistent with this finding, cells from the vaccinated mouse did bind to the OVA, but not to the LCMV tetramer spot. In addition, the cells from the control mouse failed to bind both tetramers. Taken together, this example demonstrates actual MHC-array-based detection of an immune response to a weak vaccination of a normal wild type mouse. In addition, the bound, OVA-specific cells from the vaccinated mouse were sorted out and were readily available for further analysis and/or interaction with other cells (e.g. OVA-presenting target cells).

MHC Array-based detection of human immune response to cancer vaccine (FIG. 9). A patient diagnosed with malignant melanoma currently enrolled in a peptide vaccine trial to receive gp100 (209-217), MART-1 (27-35) and tyrosinase (368-376) peptides. The patient undergoes serial peripheral blood collection on day 0 (pre-vaccine), day 14 (after peptide vaccine injection on day 0) and day 28 (post-vaccine injection on day 0 and day 14). Purified peripheral blood CD8+ T cells from day 0, day 14 and day 28, were applied to the MHC array, and incubated for 12 hrs at 4° C. The binding results indicate the development of a population of gp100 (g209-2M, 209-217)-specific CD8+ T cells at day 28 (this population was not observed on day 0 or 14). In addition, all three samples were found negative for MART1-specific and (gp100, 154-162)-specific cells.

The morphology of bound T cells, with or without their target cells can be examined by SEM (FIG. 11). In this way, high-resolution images of multiple, antigen-specific cells can be obtained. Co-immobilization of T cells with their target cells (either via the spot or via cell-cell interactions between the T cells and their targets) allows high-resolution imaging of antigen-specific cell-cell interactions.

Functional Assays with MHC-peptide Cell-arrays

Calcium flux: Using calcium flux level as a reporter, spot- and cell-type-dependent activations of lymphocytes were detected on the antibody/tetramer array (FIG. 10), demonstrating the possibility of screening for cues that activate specific lymphocyte populations and/or monitoring in real time the effects of each spot on the captured cells. OT1 and 5CC7 lymphocytes were loaded with Fura-2 for 20 minutes at room temperature, and washed with 5% FCS in RPMI ×2. A tetramer and antibody array was mounted on the stage of a fluorescent time-lapse 3D-video microscopy system, comprising a Zeiss Axiovert-100TV microscope and a Fluar 10× or 40× objective, fitted with a high-speed piezzo electric z-motor (Physik Instruments); Princeton Instruments liquid cooled CCD Interline camera (Roper Scientific) and dual excitation and emission filter wheels (Sutter Instruments); Metamorph software for microscope control, acquisition of data and image analysis (Universal Imaging).

The positions of all the spots to be viewed on the array were identified and fed into the system. The Fura-loaded cells were then applied to the array (about $1 \times 10^4$ cells in 50 µl per array block). Calcium flux levels from all pre-designated spots were monitored, as the cells were settling down onto the spots and thereafter. At each time point, the levels were determined from the 340/380 nm fluorescence ratios for each individual cell on or off specific tetramer and antibody spots. FIG. 9A shows calcium flux signal (yellow) overlaid onto a DIC image of OT1 cells on a combined α-CD3 and α-CD28 spot. The overlaid image was taken from a single frame of a time-lapse recording that starts with the layering of cells onto the array. Calcium flux signal is triggered in the OVA-specific cells as soon as they reach the OVA tetramer spots or alternatively, the activating antibody spots (e.g. α-CD3 and a combination of α-CD3 and α-CD28). In this example, the spot pattern can be inferred from the activation pattern, even without the removal of unbound cells. FIG. 9B displays averaged calcium flux profiles recorded from α-CD3+CD28 spot (yellow triangles), OVA-tetramer spot (orange circles), and α-CD3 spot (brown circles).

Induction of off-spot Binding:

Activated CTLs and helper T cells that were applied for 10-20' to arrays with activating antibodies (e.g. α-CD3 and a 1:1 mixture of α-CD3 and α-CD28) at 37° C. were induced to bind to a wide region outside the spots in addition to binding within the spots (FIG. 5). This off-spot binding was shown to be spot-specific, and doesn't occur around α-CD28 alone nor around tetramer spots that are sufficiently separated from α-CD3-containing spots; cell-type-specific (negligible for PBMCs), and temperature-dependent. At room temperature, there's almost no binding around the α-CD3 and very little binding off the α-CD3+α-CD28 spots.

Incubation of lymphocytes on the array at 37° C. appeared to lead to activation of the lymphocytes on α-CD3, and α-CD3/α-CD28 regions, leading to adherence of lymphocytes surrounding the antibody-cell immobilization zone. This effect was not observed at 4° C. and much less so at 20° C.

Exclusion of Cells:

Strong interaction between printed proteins and surface molecules on suspended cells usually leads to loading of the spots with target cells. However, on some spots we've noticed the opposite effect, whereby specific cell types being excluded from the spot area (e.g. CD4$^+$ cells on an OVA tetramer spot). This observation has been made by suspending the cells over the array (at 37° C. without washing) and following their subsequent movements in time-lapse. Exclusion (or "negative") patterns of spots becoming depleted of cells can be observed within 15-25'.

Reporter Genes:

Another realization of assaying spot-dependent activation is based on following specific intracellular re-arrangements using cells that are transduced with a reporter gene fusion construct. For example, using T cells with a GFP fused to the ζ subunit of their TCR one can follow TCR r re-arrangements (with a 40× objective) on activating spots activating spots.

What is claimed is:

1. A method of profiling T cells, the method comprising:
   contacting a cell population comprising T cells with an array, wherein said array comprises multiple discrete regions of MHC-antigen complexes stably associated with the surface of a solid planar support, and wherein an MHC-antigen complex comprises monomers or multimers of an α MHC subunit, a β MHC subunit, and a peptide antigen bound in the cleft formed by the α and β subunits;
   binding T cells to the MHC antigen complexes and
   analyzing T cells bound to the array by evaluating phenotypic attributes.

2. The method according to claim 1, wherein said array comprises a plurality of different MHC-antigen complexes.

3. A method of profiling T cells, the method comprising:
   contacting a cell population comprising T cells with an array, wherein said array comprises multiple discrete regions of MHC-antigen complexes stably associated with the surface of a solid planar support coated with polyacrylamide, and wherein an MHC-antigen complex comprises monomers or multimers of an α MHC subunit, a β MHC subunit, and a peptide antigen bound in the cleft formed by the α and β subunits;
   binding T cells to the MHC antigen complexes and
   analyzing T cells bound to the array by evaluating phenotypic attributes.

4. The method according to claim 1, wherein each of said regions comprises at least about 0.01 ng of said MHC-antigen complex.

5. The method according to claim 1, wherein each of said regions comprises a plurality of different antigenic complexes.

6. The method according to claim 1, wherein one or more of said MHC-antigen complexes comprises an antigen selected from the group consisting of tumor antigens; viral antigens, bacterial antigens; parasitic antigens; environmental antigens; allergens; and autoimmune antigens.

7. The method according to claim 1, wherein said cell population comprises multiple T cell antigenic specificities.

8. The method according to claim 1, wherein said cell population comprises multiple cell types.

9. The method according to claim 1, wherein said cell population is selected from the group consisting of blood, lymph, cerebrospinal fluid and synovial fluid.

10. The method according to claim 9, wherein said T cells are labeled with a detectable marker prior to said contacting step, and wherein said analyzing detects the presence of said marker.

11. The method according to claim 1, wherein said MHC-antigen complexes comprise a library of antigenic peptides complexed with MHC.

12. A method of profiling T cells, the method comprising:
    contacting a cell population comprising T cells with an array, wherein said array comprises multiple discrete regions of MHC-antigen complexes stably associated with the surface of a solid planar support, and wherein an MHC-antigen complex comprises monomers or multimers of an α MHC subunit, a β MHC subunit, and a peptide antigen bound in the cleft formed by the α and β subunits;
    binding T cells to the MHC antigen complexes and
    analyzing T cells bound to the array by determining a change in phenotype of said T cells after contacting with said array.

13. The method according to claim 12, wherein said change in phenotype comprises secretion of a protein in response to antigenic stimulation.

14. A method of profiling T cells the method comprising:
    contacting a cell population comprising T cells with an array, wherein said array comprises multiple discrete regions of MHC-antigen complexes stably associated with the surface of a solid planar support, wherein one or more of said discrete regions present on said array comprise cells and MHC-antigen complexes, and wherein an MHC-antigen complex comprises monomers or multimers of an α MHC subunit, a β MHC subunit, and a peptide antigen bound in the cleft formed by the α and β subunits;
    binding T cells to the MHC antigen complexes and
    analyzing T cells bound to the array by evaluating phenotypic attributes.

15. The method according to claim 14, wherein said cells are antigen presenting cells.

16. The method according to claim 1, further comprising the step of contacting said array with a second cell population, and determining the binding of cells present in said second cell population to said T cells bound to the array.

17. The method according to claim 1, further comprising the step of contacting said array with a second cell population, and determining a change in the phenotype of said T cells bound to the array.

18. The method of claim 1, further comprising the step of determining the expression of cell surface antigens by said T cells following said contacting step.

19. The method according to claim 1, further comprising the step of releasing said cells from said array.

20. The method according to claim 1, further comprising the step of expanding said T cells following said contacting step.

21. The method according to claim 20, wherein said expanding step comprises contacting said T cells with one or more of growth factors, cytokines, cell adhesion molecules, and extracellular matrix material.

22. The method according to claim 1, wherein said array comprises a plurality of spots having differing concentrations of MHC-antigen complexes.

23. The method according to claim 22, further comprising the step of constructing a scaling curve for binding of T cells to said MHC-antigen complexes.

24. The method according to claim 1, further comprising the step of determining binding of said cells to said MHC antigen complexes in a site specific analysis.

* * * * *

UNITED STATES PATENT AND TRADEMARK OFFICE
CERTIFICATE OF CORRECTION

| | | |
|---|---|---|
| PATENT NO. | : 7,902,121 B2 | Page 1 of 1 |
| APPLICATION NO. | : 10/856185 | |
| DATED | : March 8, 2011 | |
| INVENTOR(S) | : Chen et al. | |

It is certified that error appears in the above-identified patent and that said Letters Patent is hereby corrected as shown below:

In The Specification Under Column 1:

• Please insert at line 1:

-- FEDERALLY-SPONSORED RESEARCH OR DEVELOPMENT
This invention was made with Government support under contract AI22511 awarded by the National Institutes of Health. The Government has certain rights in this invention. --

Signed and Sealed this
Twenty-first Day of May, 2013

Teresa Stanek Rea
*Acting Director of the United States Patent and Trademark Office*